(12) United States Patent
Hill

(10) Patent No.: US 7,249,948 B2
(45) Date of Patent: Jul. 31, 2007

(54) ERGONOMIC DENTAL INSTRUMENTS FOR SMALL HANDS

(75) Inventor: Elizabeth J. Hill, Morrison, CO (US)

(73) Assignee: Chapin Hill Instrument Company, LLC, Littleton, CO (US)

(*) Notice: Subject to any disclaimer, the term of this patent is extended or adjusted under 35 U.S.C. 154(b) by 77 days.

(21) Appl. No.: 11/197,794

(22) Filed: Aug. 4, 2005

(65) Prior Publication Data

US 2006/0029906 A1   Feb. 9, 2006

Related U.S. Application Data

(60) Provisional application No. 60/599,496, filed on Aug. 6, 2004.

(51) Int. Cl.
*A61C 17/00* (2006.01)

(52) U.S. Cl. .................................. 433/143; 433/141

(58) Field of Classification Search ............ 433/141, 433/142, 143, 144, 72
See application file for complete search history.

(56) References Cited

U.S. PATENT DOCUMENTS

| | | | | |
|---|---|---|---|---|
| 1,742,040 A | * | 12/1929 | Lynch et al. .............. | 173/93.7 |
| 2,248,054 A | * | 7/1941 | Becker ....................... | 81/457 |
| 2,808,055 A | * | 10/1957 | Thayer ....................... | 606/144 |
| 4,541,992 A | | 9/1985 | Jerge et al. | |
| 4,552,531 A | * | 11/1985 | Martin ....................... | 433/147 |
| D295,074 S | | 4/1988 | Jerge et al. | |
| D295,075 S | | 4/1988 | Jerge et al. | |
| 4,854,475 A | | 8/1989 | Riihimaki et al. | |
| D320,076 S | | 9/1991 | Guthrie | |
| 5,161,971 A | | 11/1992 | Neiner et al. | |
| 5,169,313 A | * | 12/1992 | Kline ....................... | 433/143 |
| D335,347 S | | 5/1993 | McKeown | |
| D336,517 S | | 6/1993 | McKeown | |
| 5,215,726 A | | 6/1993 | Kudla et al. | |
| 5,256,064 A | | 10/1993 | Riihimaki et al. | |
| D342,446 S | | 12/1993 | Parker et al. | |
| 5,284,632 A | | 2/1994 | Kudla et al. | |
| 5,294,413 A | | 3/1994 | Riihimaki et al. | |
| D360,697 S | | 7/1995 | Riihimaki et al. | |
| 5,433,929 A | | 7/1995 | Riihimaki et al. | |
| 5,624,259 A | * | 4/1997 | Heath et al. .............. | 433/72 |
| D394,902 S | | 6/1998 | Herbst et al. | |
| 5,775,901 A | | 7/1998 | Riso | |
| 5,816,806 A | | 10/1998 | Herbst et al. | |
| D425,202 S | | 5/2000 | Hammond et al. | |

(Continued)

OTHER PUBLICATIONS

Anne Nugent Guignon, RDG, MPH, Instrument Design, *Understanding the File Details*, RDH/Jul. 2005.

*Primary Examiner*—Ralph A. Lewis
(74) *Attorney, Agent, or Firm*—Townsend and Townsend and Crew LLP

(57) ABSTRACT

The invention provides systems and methods for ergonomic dental instruments for dental professionals with small hands. In one embodiment, a dental instrument includes an elongated metal handle having a length in the range of about 3-7/16 inches to about 3-15/16 inches and a diameter in the range of about 1/4 inches to about 3/4 inches. A working end may be operably coupled to one or both ends of the handle via a sweated fit. The length and knurling of the elongated metal shaft and terminal shaft facilitate optimum performance for the user.

30 Claims, 12 Drawing Sheets

U.S. PATENT DOCUMENTS

| | | |
|---|---|---|
| 6,109,918 A | 8/2000 | Hammond et al. |
| D441,457 S | 5/2001 | Neiner et al. |
| 6,309,219 B1 * | 10/2001 | Robert ........................ 433/144 |
| 6,322,362 B1 * | 11/2001 | Holms ......................... 433/143 |
| 6,361,317 B1 | 3/2002 | Rahman |
| 6,471,514 B2 * | 10/2002 | Beck et al. .................. 433/141 |
| 6,716,028 B2 | 4/2004 | Rahman et al. |
| 6,729,877 B2 | 5/2004 | Rahman |

* cited by examiner

ERGONOMIC DENTAL INSTRUMENTS FOR SMALL HANDS

CROSS-REFERENCES TO RELATED APPLICATIONS

The present application claims the benefit under 35 U.S.C. § 119(e) of U.S. Provisional Application No. 60/599,496 filed Aug. 6, 2004, the contents of which are incorporated herein by reference.

FIELD OF THE INVENTION

The present invention relates generally to dental instruments. More particularly, the present invention provides small-handed dental professionals with ergonomic dental instruments that prevent serious injury and reduce hand, wrist and arm fatigue during hygiene, diagnostic and restorative treatments.

BACKGROUND OF THE INVENTION

There is a large range of hand-held dental instruments available for the removal of supra and subgingival calculus, including ultrasonic devices, probes, explorers, curettes, sickles, hoes, files and chisels. Such hand-held dental instruments have long been known and are useful in connection with dental hygiene as well as diagnostic and restorative treatments.

The overall size of hand-held dental instruments has not changed significantly since their invention in the 1930's. The size of dental instruments was originally designed with a large handed person in mind, since most dental professionals were men. A clinician with larger hands could not fit his fingers inside the patient's mouth, so the handle and instrument end had to be longer. In this way, the professional could place his fingers on the exterior of the mouth to establish the fulcrum to work on the patient's teeth. Presently, larger sized instruments are not optimal for clinicians with small hands.

In recent years, dental practice has shifted toward an ergonomic focus. A few examples of ergonomic advancement in the dentistry field include new operator stool designs that include arm rests, magnification loupes that improve visibility while optimizing posture and new instrument handles with scoring patterns and larger diameter handles. Much has been written about cumulative trauma disorders (CTD), yet these injuries continue to be problematic for dental professionals. In some cases, despite costly and painful treatment, the pain and dysfunction return. CTD can affect daily life, from simple tasks like holding the telephone to recreational activities like gardening or knitting. CTD affects everything that requires good hand dexterity.

Cumulative trauma disorders include work-related musculoskeletal disorders, repetitive motion injury/disorders, and repetitive strain injuries. These injuries can affect the nerves, tendons, and neurovasculature of upper extremities and thus gravely impact the ability to practice in the dental field.

In particular, there is a high prevalence of carpal tunnel syndrome among dental practitioners. Periodontal procedures, such as scaling and root planing, practiced by both dentists and dental hygienists, are among the high-risk tasks. Currently, non-powered hand instruments are still important in performing these tasks. Studies on instrument handle designs indicate that handles have a strong effect on operator performance and muscle stress. It is therefore crucial to design ergonomic hand instruments for dental professionals with small hands to reduce operator muscle load during dental procedures. Preferably, such instruments will be easy to pick up and use, and will include features to minimize fatigue and injuries when the instruments are in use.

BRIEF SUMMARY OF THE INVENTION

The invention provides for various dental instruments for small handed dental clinicians as well as methods for their use. The dental instruments have an elongated metal handle having a first end and a second end. In some cases, the handle has a length between $3^{7}/_{16}$ inches to about $3^{15}/_{16}$ inches. In some cases, the diameter of the handle lies within a range of about $1/4$ inches to about $3/4$ inches.

The dental instrument has a first terminal shaft having a front end and a back end. The terminal shaft has a knurling pattern extending from the front end to the back end that improves the grip on the dental instrument. The terminal shaft has an angle $\alpha$ formed between a line extending along and out of the handle and a line extending along the terminal shaft from the back end to the front end.

In one aspect, the dental instrument includes a terminal shank secured to the front end of the terminal shaft. In certain embodiments, the terminal shank may be secured to the terminal shaft via a tapered sweated fit and, optionally, via the use of a fixative. In some embodiments, the dental instrument also may include a working end metallically secured to the terminal shank. The working end provides an instrument for cleaning or repairing a tooth.

In other aspects of the invention, methods for attaching dental instrument tips to dental instrument handles are also provided, as well as methods of using dental instruments described herein.

These and other aspects will be understood by those skilled in the art with reference to the detailed description and drawings herein.

DETAILED DESCRIPTION OF THE INVENTION

Figure 1:
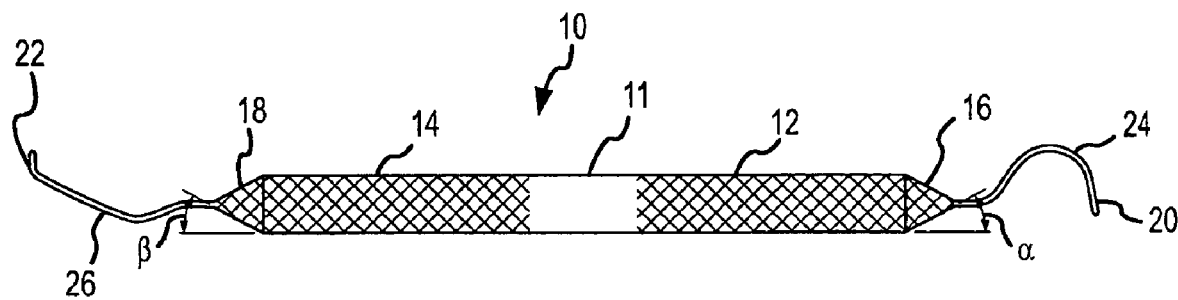
FIG. 1 is a front view of a #15 Explorer dental instrument in accordance with one embodiment of the present invention.

Described below are several exemplary embodiments of the invention. Although certain features are described, for ease of discussion, in relation to certain illustrated embodiments, those skilled in the art will appreciate, based on the disclosure herein, that various of the inventive features can be combined in accordance with many different embodiments of the invention. The illustrated embodiments below, therefore, are provided merely by way of example and should not be considered to limit the scope of the invention, which is defined only by the appended claims.

The invention provides a wide variety of dental instruments that each include a handle. One important aspect of the invention is the sizing of the handle length to be in the range of about $3^{7}/_{16}$ inches to about $3^{15}/_{16}$ inches, in certain embodiments in the range of about 3.6 inches to about 3.9 inches, more preferably about 3.73 inches for anterior applications and 3.85 for posterior applications. The handle diameter of the same instrument may be in the range of about ¼ inches to about ¾ inches, in certain embodiments in the range of about 0.25 to about 0.50, more preferably about 0.36 inches. The particular choice in size of the handle allows the instruments to be used more efficiently by small-handed dental clinicians. The fingers of a small hand actually fit inside the mouth of a patient and thus the handle and end portion of a dental instrument does not have to be as long as the instruments currently available and used by a dental professional with larger hands and fingers. Such an ergonomic solution provides benefits such as reducing insurance premiums, spending less time and employing less muscle energy "walking down" the handle, sterilizing more instruments in an autoclave, inexpensively manufacturing the instruments, reducing hand fatigue, increasing joint stability, reducing the amount and severity of hand, wrist and arm injuries leading to an increased length of time to practice in the dental field.

Another important aspect of the invention provides apparatus and methods for ergonomic dental instruments that reduces the risk of Repetitive Strain Injuries (RSI) like Carpal Tunnel Syndrome (CTS) for small-handed dental professionals. The invention is best applied to alleviate hand fatigue for clinicians with small hands, allowing the clinician to grasp the instrument with ease and confidence. The critical working stroke is made more efficient through a positive control of the dental instrument, while preventing fatigue to the dental professional's fingers, hands and arms.

One particular advantage of the invention is the maintenance of a neutral wrist position. Since the clinician's hands experience less fatigue, the over all body dynamics also benefit. By establishing and maintaining a neutral wrist position, the clinician's posture improves reducing stress and fatigue of both the neck and shoulders.

Another advantage of the invention is the allowance of superior balance and tactile sensitivity. A continuous vibration travels from the working end of the instrument, through the shank, through the terminal shaft and into the handle that is held in a dental professional's fingertips. Due to the tapered sweat fit feature, as described more fully hereinafter, this attachment method provides an increase in the strength or "fidelity" of this engagement over typical instruments.

Yet another advantage of the invention is the ability to "flip" an instrument away from the patient and not have to walk as far down the handle to use the second working end. The longer the handle, the more stress applied to the main tendon in the forearm and wrist. A shortened handle not only reduces the amount of stress the main tendon is exposed to but also allows the clinician to see more patients over the course of the workday.

In another aspect, yet another advantage of the invention relates to the tip to handle interface of the dental instrument, which allows for repeated autoclaving without significant loss of engagement between parts. In this regard, the instrument tip may be securely engaged with the handle of the dental instrument via a tapered sweated fit, achieved by a temperature differential between the mating parts. This method generally requires a close tolerance between the two, interfering parts, and the securing mechanism occurs via small variations in size of mating parts due to heating one and cooling (or not heating) the other. As the parts come to a common temperature, the tolerances converge, and the parts mate to form a sweated fit.

As will be recognized by those skilled in the art, aluminum plated parts, as often for the handles of dental instrumentation, do not easily lend themselves to the tight tolerances needed for sweated fittings. To address such considerations, the present invention provides a handle with end portions that comprise terminal shafts adapted for such purposes, as described in further detail below.

I. Hygiene Dental Instruments

FIGS. 1-19 illustrate various dental hygiene dental instruments in accordance with aspects of the present invention. In describing the instruments in FIGS. 1-19, it will be appreciated that the manner of attaching the functional shanks to the handles may be achieved using the techniques described in connection with FIGS. 32-35.

FIG. 1 illustrates a #15 Explorer 10 in accordance with the present invention. In operation, Explorer 10 is used to indicate tooth decay, faulty margins in composite fillings, amalgam fillings and crowns by touch. Explorer 10 has a handle 11 with a knurling pattern 12, 14 integrated into each end of the handle 11. A first terminal shaft 16 is located at a first end of handle 11 and a second terminal shaft 18 is located at a second end of handle 11. Shank 24 is securely engaged to terminal shaft 16 and shank 26 is securely engaged to terminal shaft 18. Working end 20 is coupled to shank 24 and working end 22 is coupled to shank 26. The combination of terminal shaft 16, working end 20 and shank 24 make up a first end portion. The combination of terminal shaft 18, working end 22 and shank 26 make up a second end portion.

Working ends 20, 22 are the part of a dental instrument that does the work of the instrument. Working ends 20, 22 begin where the instrument shanks 24, 26 end. Shanks 24, 26 are circular and smooth, but working ends 20, 22 are shaped or flattened on some of its surfaces. Working ends 20, 22 may terminate in a sharp point. It may be thin and wirelike, or look somewhat like a tiny measuring stick. An instrument may have one or two working-ends.

A functional shank is defined by the area extending from the tip of working ends 20, 22 to last bend on shanks 24, 26, which occurs immediately after terminal shafts 16, 18. In certain embodiments, the functional shank may extend within terminal shaft 16, 18 to thereby securely engage the functional shank to the terminal shaft 16, 18 (not shown). A terminal shank is defined by the area beginning below working ends 20, 22 extending to the first bend after terminal shafts 16, 18 respectively. Again, the terminal shank may extend within the terminal shaft 16, 18 to thereby securely engage the functional shank to the terminal shaft 16, 18 (not shown). In operation, short functional shanks are used on coronal surfaces and long functional shanks are used on coronal and root surfaces. The shape and rigidity of shanks 24, 26 determine access of working end 20, 22 for its use. Working ends 20, 22 define the use and function of the Explorer 10.

Terminal shafts 16, 18 have a knurling pattern that extends from the a mid portion of handle 11 to shanks 24, 26 respectively. The knurling pattern on terminal shafts 16, 18 improves the dental professional's grip on the Explorer 10. An angle $\alpha$ is formed between a line extending from the back end to the front end of terminal shaft 16 and a line extending from handle 11. Angle $\alpha$ ranges from about 5 degrees to about 45 degrees, more preferably from about 5 degrees to about 15 degrees and in one option about 10 degrees. An angle $\beta$ is formed between a line extending from the back end to the front end of terminal shaft 18 and a line extending from handle 11. Angle $\beta$ ranges from about 5 degrees to about 45 degrees, more preferably from about 5 degrees to about 15 degrees and in one option about 10 degrees.

The weight, diameter, handle length and surface texture of Explorer 10 contributes to its ergonomic properties. Preferably, handle 11 of Explorer 10 is hollow since a hollow handle is lighter, resulting in less fatigue and increased intensity of vibrations to fingers of the dental professional. Handle 11 may also be a solid metal without reducing the effectiveness of the ergonomic properties of the present invention. A large diameter of handle 11 is easier to control reducing muscle cramps. A surface of handle 11 having grooves and ridges is easier to control and lends itself to less repetitive stress injury.

The length of handle 11 of Explorer 10 is in the range of about 3 7/16 inches to about 3 15/16 inches, in certain embodiments in the range of about 3.6 inches to about 3.9 inches, more preferably about 3.85 inches. Handle 11 has a diameter that ranges from about ¼ inches to about ¾ inches, in certain embodiments in the range of about 0.25 to about 0.50, more preferably about 0.36 inches. The length of the functional shank from the front of terminal shaft 16 to the end of working end 20 measured along a center line extending from the center of handle 11 may fall in a range from about 15/16 inches to about 1 3/16 inches, and is preferably about one inch. The length of the functional shank from the front of terminal shaft 18 to the end of working end 22 measured along a center line extending from the center of handle 11 may fall in a range from about 15/16 inches to about 1 3/16 inches, and is preferably about one inch.

The firm but light hold a dental clinician has on their instruments is referred to as "grasp." A proper grasp enables the clinician to maneuver the instrument around the tooth and correctly direct pressure application for calculus removal without damaging the periodontal tissues. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 11 of Explorer 10 at the knurling pattern 12, 14 molded into handle 11 using a modified pen grasp. The thumb and index finger of the clinician are at an opposing position on the handle 11 at junction of handle 11 and terminal shaft 16, 18. Handle 11 is between junction of the first and second joint of the index finger. The pad of the middle finger rests against the shank 24, 26 (side of pad). The fingers of the clinician operate as a "unit."

Continuing with the operation of Explorer 10, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke. Configuration of Explorer 10 as well as the other instruments described herein facilitates such uses.

Figure 2:
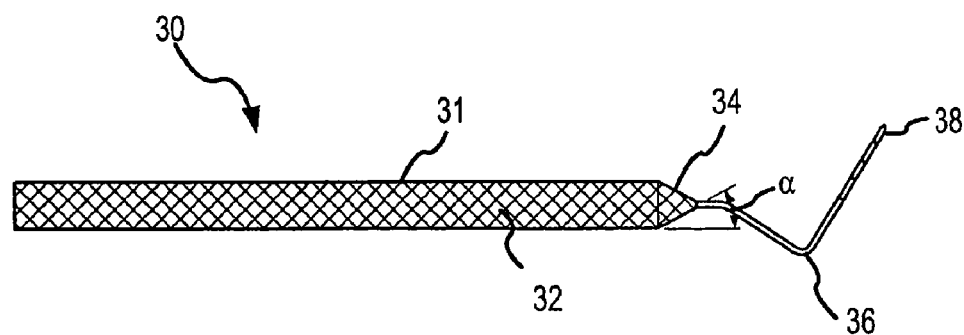
FIG. 2 is a front view of a Probe 3-6-9-12 dental instrument in accordance with another embodiment of the present invention.

FIG. 2 illustrates a Probe 3-6-9-12 30 in accordance with the present invention. Probe 3-6-9-12 30 is the primary instrument in the periodontal exam for assessing gingival health and periodontal status. In operation, Probe 3-6-9-12 30 is inserted to the junctional epithelium to measure sulcus, periodontal pockets, gingival recession and attachment loss as well as depth of bone level around the gumline. Typically, Probe 3-6-9-12 30 is color coded with 3, 6, 9, 12 mm markings.

Probe 3-6-9-12 30 has a handle 31 with a knurling pattern 32, 14 molded into each end of the handle 11. A terminal shaft 34 is located at a first end of handle 31. Shank 36 is securely engaged to terminal shaft 34. Working end 38 is coupled to shank 36. The combination of terminal shaft 34, working end 38 and shank 36 make up an end portion. A functional shank is defined by the area extending from the tip of working end 38 to last bend on shank 36, which occurs immediately before terminal shaft 34. In an alternative embodiment, the functional shank may extend into terminal shaft 34 to thereby securedly engage the function shank to terminal shaft 34 (not shown). A terminal shank is defined by the area beginning below working end 38 extending to the first bend after terminal shaft 34. Again, the terminal shank may alternatively extend into terminal shaft 34 to thereby securedly engage the function shank to terminal shaft 34 (not shown). In operation, short functional shanks are used on coronal surfaces and long functional shanks are used on coronal and root surfaces. The shape and rigidity of terminal shank 36 determine access of working end 38 for its use. Working end 38 defines the use and function of the Probe 3-6-9-12 30.

Terminal shaft 34 has a knurling pattern that extends from a midrange portion on handle 31 to shank 36. The knurling pattern on terminal shaft 34 improves the dental professional's grip on the Probe 30. An angle α is formed between a line extending from the back end to the front end of terminal shaft 34 and a line extending along and outward from handle 31. Angle α ranges from about 5 degrees to about 45 degrees, more preferably from about 5 degrees to about 15 degrees and in one option about 10 degrees.

The weight, diameter, handle length and surface texture of Probe 30 contributes to its ergonomic properties. Preferably, handle 31 of Probe 30 is hollow, because a hollow handle is lighter, resulting in less fatigue and increased intensity of vibrations to fingers of the dental professional. Handle 31 may also be a solid metal without reducing the effectiveness of the ergonomic properties of the present invention. A large diameter of handle 31 is easier to control reducing muscle cramps. A surface of handle 11 having grooves and ridges is easier to control and lends itself to less repetitive stress injury.

The length of handle 31 of Probe 30 is in the range of about 3 inches to about $3^{15}/_{16}$ inches, in certain embodiments in the range of about 3.6 inches to about 3.9 inches, more preferably about 3.85 inches. In other embodiments, handle 31 is in the range of about $3^{7}/_{16}$ inches to about $3^{11}/_{16}$ inches. Handle 31 has a diameter that ranges from about ¼ inches to about ¾ inches, in certain embodiments in the range of about 0.25 to about 0.50, more preferably about 0.36 inches. The length of the functional shank from the front of terminal shaft 34 to the end of working end 38 measured along a center line extending from the center of handle 31 may fall in a range from about 1 inch to about $1^{3}/_{16}$ inches, and may be about 1¼ inch.

Figure 3:
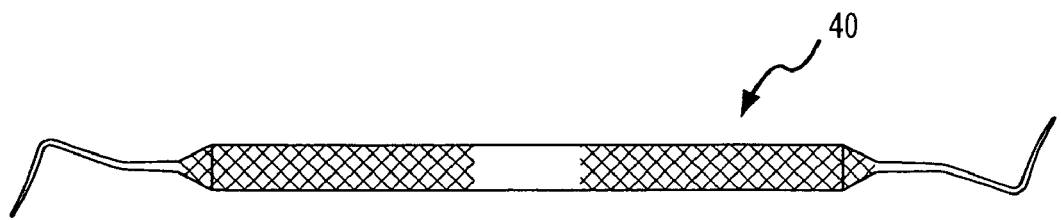
FIG. 3 is a front view of a #2 Explorer dental instrument in accordance with another embodiment of the present invention.
Figure 4:
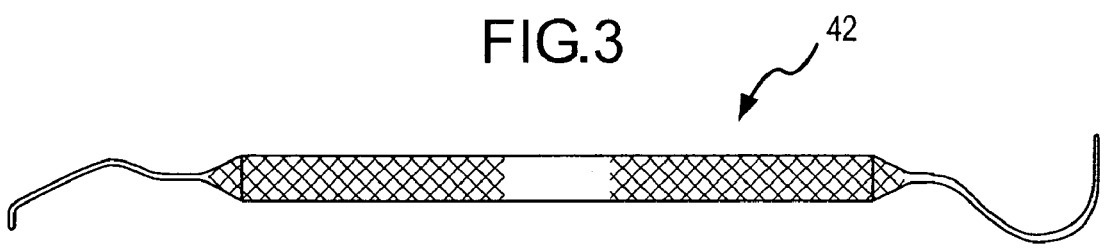
FIG. 4 is a front view of a #5 Explorer dental instrument in accordance with another embodiment of the present invention.

FIG. 3 illustrates a #2 Explorer 40 and FIG. 4 illustrates a #5 Explorer 42 in accordance with the present invention. The description, use and dimensions for both #2 Explorer 42 and #5 Explorer 44 are identical to the description, use and dimensions for the #15 Explorer 10 of FIG. 1 and therefore will not be repeated.

Figure 5:
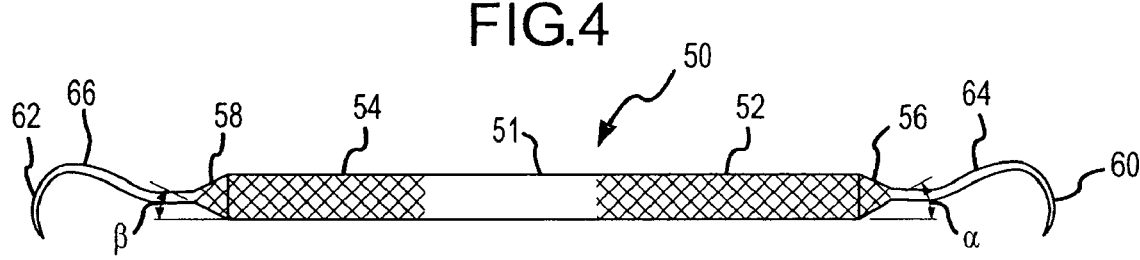
FIG. 5 is a front view of a Sickle #6 dental instrument in accordance with another embodiment of the present invention.

FIG. 5 illustrates a Sickle #6 50 in accordance with the present invention. In operation, Sickle 50 removes heavy calculus supragingivally. Sickle 50 will reach along the crown and root surface. Sickle 50 has a handle 51 with a knurling pattern 52, 54 molded into each end of the handle 51. A first terminal shaft 56 is located at a first end of handle 51 and a second terminal shaft 58 is located at a second end of handle 51. Shank 54 is securely engaged to terminal shaft 56 and shank 66 is securely engaged to terminal shaft 58. Working end 60 is coupled to shank 64 and working end 62 is coupled to shank 66. The combination of terminal shaft 56, working end 60 and shank 64 make up a first end portion. The combination of terminal shaft 58, working end 62 and shank 66 make up a second end portion.

A functional shank is defined by the area extending from the tip of working ends 60, 62 to last bend on shanks 64, 66, which occurs immediately after terminal shafts 56, 58. In an alternative embodiment, the functional shank may extend into terminal shaft 56, 58 to thereby securedly engage the function shank to terminal shaft 56, 58 (not shown). A terminal shank is defined by the area beginning below working ends 60, 62 extending to the first bend after terminal shafts 56, 58 respectively. Again, the terminal shank may alternatively extend into terminal shaft 56, 58 to thereby securedly engage the function shank to terminal shaft 56, 58 (not shown). In operation, short functional shanks used on coronal surfaces and long functional shanks used on coronal and root surfaces. The shape and rigidity of shanks 64, 66 determine access of working end 60, 62 for its use. Working ends 60, 62 define the use and function of the Sickle 50.

Terminal shafts 56, 58 have a knurling pattern that extends from a midpoint on the handle 51 to shanks 64, 66 respectively. The knurling pattern on terminal shafts 56, 58 improves the dental professional's grip on the Sickle 50. An angle α is formed between a line extending from the back end to the front end of terminal shaft 56 and a line extending from handle 51. Angle α ranges from about 5 degrees to about 45 degrees, more preferably from about 5 degrees to about 15 degrees and in one option about 10 degrees. An angle β is formed between a line extending from the back end to the front end of terminal shaft 58 and a line extending from handle 51. Angle β ranges from about 5 degrees to about 45 degrees, more preferably from about 5 degrees to about 15 degrees and in one option about 10 degrees.

The weight, diameter, handle length and surface texture of Sickle 50 contribute to its ergonomic properties. Preferably, handle 51 of Sickle 50 is hollow since a hollow handle is lighter, resulting in less fatigue and increased intensity of vibrations to fingers of the dental professional. Handle 51 may also be a solid metal without reducing the effectiveness of the ergonomic properties of the present invention. A large diameter of handle 51 is easier to control reducing muscle cramps. A surface of handle 51 having grooves and ridges is easier to control and lends itself to less repetitive stress injury.

The length of handle 51 of Sickle 50 is in the range of about 3 7/16 inches to about 3 15/16 inches, in certain embodiments in the range of about 3.6 inches to about 3.9 inches, more preferably about 3.73 inches. Handle 51 has a diameter that ranges from about ¼ inches to about ¾ inches, in certain embodiments in the range of about 0.25 to about 0.50, more preferably about 0.36 inches. The length of the functional shank from the front of terminal shaft 56 to the end of working end 60 measured along a center line extending from the center of handle 51 may fall in a range from about ⅞ inches to about 1½ inches, and may be about 1 inch. The length of the functional shank from the front of terminal shaft 58 to the end of working end 62 measured along a center line extending from the center of handle 51 falls in a range from about ⅞ inches to about 1½ inches, and is preferably about 1 inch.

The firm but light hold a dental clinician has on their instruments is referred to as "grasp." A proper grasp enables the clinician to maneuver the instrument around the tooth and correctly direct pressure application for calculus removal without damaging the periodontal tissues. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 51 of Sickle 50 at the knurling pattern 52, 54 molded into handle 51 using a modified pen grasp. The thumb and index finger of the clinician are at an opposing position on the handle 51 at junction of handle 51 and terminal shaft 56, 58. Handle 51 is between junction of the first and second joint of the index finger. The pad of the middle finger rests against the shank 64, 66 (side of pad). The fingers of the clinician operate as a "unit."

Continuing with the operation of Sickle 50, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke. Configuration of Sickle 50 in the manner described facilitates such users.

Figure 6:
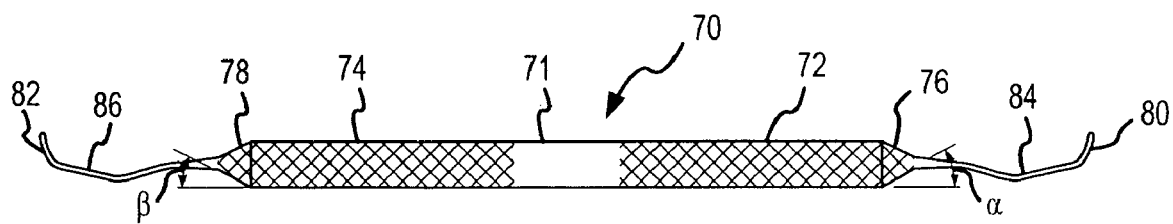
FIG. 6 is a front view of a Gracey 1/2 dental instrument in accordance with another embodiment of the present invention.

FIG. 6 illustrates a Gracey 1/2 70 in accordance with the present invention. In operation, Gracey 70 removes heavy calculus supragingivally. A Gracey in general is designed to provide better access to root surfaces in deep pockets. Each features long shanks and unique blades, some with bends improving access to complex root surface morphology. Gracey Curette 1/2 70 is used to scale all tooth surfaces in the anterior sextants.

Gracey 70 has a handle 71 with a knurling pattern 72, 74 molded into each end of the handle 71. A first terminal shaft 76 is located at a first end of handle 71 and a second terminal shaft 78 is located at a second end of handle 71. Shank 84 is securedly engaged to terminal shaft 76 and shank 86 is securedly engaged to terminal shaft 78. Working end 80 is coupled to shank 84 and working end 82 is coupled to shank 86. The combination of terminal shaft 76, working end 80 and shank 84 make up a first end portion. The combination of terminal shaft 78, working end 82 and shank 86 make up a second end portion.

A functional shank is defined by the area extending from the tip of working ends 80, 82 to last bend on shanks 84, 86, which occurs immediately after terminal shafts 76, 78. In an alternative embodiment, the functional shank may extend into terminal shaft 76, 78 to thereby securedly engage the function shank to terminal shaft 76, 78 (not shown). A terminal shank is defined by the area beginning below working ends 80, 82 extending to the first bend after terminal shafts 76, 78 respectively. Again, the terminal shank may alternatively extend into terminal shaft 76, 78 to thereby securedly engage the function shank to terminal shaft 76, 78 (not shown). In operation, short functional shanks used on coronal surfaces and long functional shanks used on coronal and root surfaces. The shape and rigidity of shanks 74, 76 determine access of working end 80, 82 for its use. Working ends 80, 82 define the use and function of the Gracey 70.

Terminal shafts 76, 78 have a knurling pattern that extends from a midpoint on the handle 71 to shanks 84, 86 respectively. The knurling pattern on terminal shafts 76, 78 improves the dental professional's grip on the Gracey 70. An angle α is formed between a line extending from the back end to the front end of terminal shaft 76 and a line extending from handle 71. Angle β ranges from about 5 degrees to about 45 degrees, more preferably from about 5 degrees to about 15 degrees and in one option about 10 degrees. An angle β is formed between a line extending from the back end to the front end of terminal shaft 78 and a line extending from handle 71. Angle β ranges from about 5 degrees to about 45 degrees, more preferably from about 5 degrees to about 15 degrees and in one option about 10 degrees.

The weight, diameter, handle length and surface texture of Gracey 70 contribute to its ergonomic properties. Preferably, handle 71 of Gracey 70 is hollow since a hollow handle is lighter, resulting in less fatigue and increased intensity of vibrations to fingers of the dental professional. Handle 71 may also be a solid metal without reducing the effectiveness of the ergonomic properties of the present invention. A large diameter of handle 71 is easier to control reducing muscle cramps. A surface of handle 71 having grooves and ridges is easier to control and lends itself to less repetitive stress injury.

The length of handle 71 of Gracey 70 is in the range of about 3 7/16 inches to about 3 15/16 inches, in certain embodiments in the range of about 3.6 inches to about 3.9 inches, more preferably about 3.73 inches. Handle 71 has a diameter that ranges from about ¼ inches to about ¾ inches, in certain embodiments in the range of about 0.25 to about 0.50, more preferably about 0.36 inches. The length of the functional shank from the front of terminal shaft 76 to the end of working end 80 measured along a center line extending from the center of handle 71 may fall in a range from about ⅞ inches to about 1½ inches, and may be about 1 inch. The length of the functional shank from the front of terminal shaft 78 to the end of working end 82 measured along a center line extending from the center of handle 71 may fall in a range from about ⅞ inches to about 1½ inches, and is may be about 1 inch.

The firm but light hold a dental clinician has on their instruments is referred to as "grasp." A proper grasp enables the clinician to maneuver the instrument around the tooth and correctly direct pressure application for calculus removal without damaging the periodontal tissues. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 71 of Gracey 70 at the knurling pattern 72, 74 molded into handle 71 using a modified pen grasp. The thumb and index finger of the clinician are at an opposing position on the handle 71 at junction of handle 71 and terminal shaft 76, 78. Handle 71 is between junction of the first and second joint of the index finger. The pad of the middle finger rests against the shank 84, 86 (side of pad). The fingers of the clinician operate as a "unit."

Continuing with the operation of Gracey 70, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke.

Figure 7:
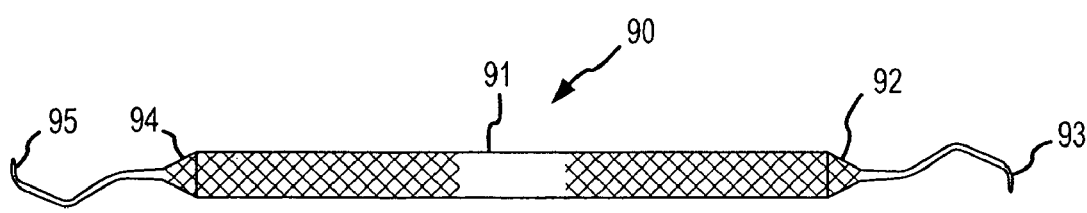
FIG. 7 is a front view of a Gracey 7/8 dental instrument in accordance with another embodiment of the present invention.
Figure 8:
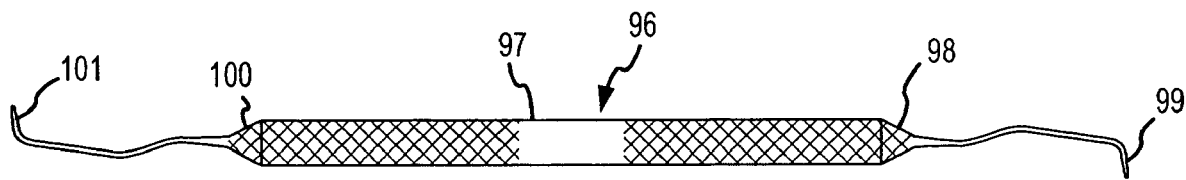
FIG. 8 is a front view of a Gracey 11/12 dental instrument in accordance with another embodiment of the present invention.
Figure 9:
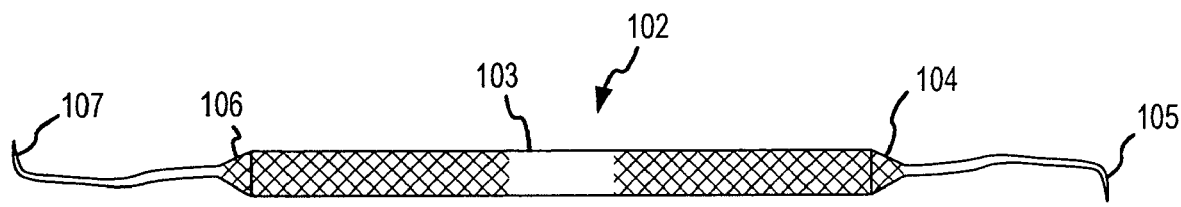
FIG. 9 is a front view of a Gracey 13/14 dental instrument in accordance with another embodiment of the present invention.
Figure 10:
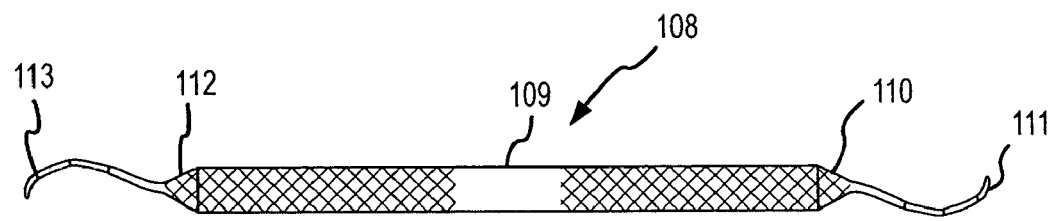
FIG. 10 is a front view of a #15/16 Gracey Curette dental instrument in accordance with another embodiment of the present invention.
Figure 11:
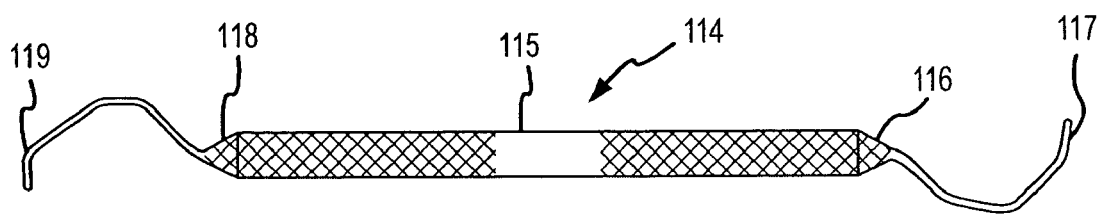
FIG. 11 is a front view of a #17/18 Gracey Curette dental instrument in accordance with another embodiment of the present invention.

FIG. 7 illustrates a Gracey 7/8 90, FIG. 8 illustrates a Gracey 11/12 92, FIG. 9 illustrates a Gracey 13/14 94, FIG. 10 illustrates a #15/16 Gracey Curette 96 and FIG. 11 illustrates a #17/18 Gracey Curette 98 in accordance with the present invention. The description for each is identical to the Gracey 1/2 illustrated in FIG. 6 and will not be repeated. The dimensions and use of each are different and therefore are described in further detail.

Gracey Curettes 7/8 90 is used for scaling the buccal and lingual aspects of teeth in the posterior sextants. Gracey Curette 11/12 96 and Gracey Curette 15/16 108 are used to scale the mesial aspects of the teeth in the posterior sextant. Gracey Curette 13/14 102 and Gracey Curette 17/18 114 are used to scale the distal aspects. Gracey instruments also may be obtained in 3/4 configurations (not shown).

In FIG. 7, the length of handle 91 of Gracey 7/8 90 is in the range of about 3 7/16 inches to about 3 15/16 inches, in certain embodiments in the range of about 3.6 inches to about 3.9 inches, more preferably about 3.85 inches. Handle 91 has a diameter that ranges from about ¼ inches to about ¾ inches, in certain embodiments in the range of about 0.25 to about 0.50, more preferably about 0.36 inches. The length of the functional shank from the front of terminal shaft 92 to the end of working end 93 measured along a center line extending from the center of handle 91 may fall in a range from about 1⅛ inches to about 1½ inches, and may be about 1¼ inch. The length of the functional shank from the front of terminal shaft 94 to the end of working end 95 measured along a center line extending from the center of handle 91 may fall in a range from about 1⅛ inches to about 1½ inches, and may be about 1¼ inch.

As shown in FIG. 8, the length of handle 97 of Gracey 11/12 96 is in the range of about 3 7/16 inches to about 3 15/16 inches, in certain embodiments in the range of about 3.6 inches to about 3.9 inches, more preferably about 3.85 inches. Handle 97 has a diameter that ranges from about ¼ inches to about ¾ inches, in certain embodiments in the range of about 0.25 to about 0.50, more preferably about 0.36 inches. The length of the functional shank from the front of terminal shaft 98 to the end of working end 99 measured along a center line extending from the center of handle 97 may be about 1¼ inch. The length of the functional shank from the front of terminal shaft 100 to the end of working end 101 measured along a center line extending from the center of handle may be about 1¼ inch.

As shown in FIG. 9, the length of handle 103 of Gracey 13/14 102 is in the range of about 3⅞ inches to about 3¹⁵⁄₁₆ inches, in certain embodiments in the range of about 3.6 inches to about 3.9 inches, more preferably about 3.85 inches. Handle 103 has a diameter that ranges from about ¼ inches to about ¾ inches, in certain embodiments in the range of about 0.25 to about 0.50, more preferably about 0.36 inches. The length of the functional shank from the front of terminal shaft 104 to the end of working end 105 measured along a center line extending from the center of handle 103 may be about 1¼ inch. The length of the functional shank from the front of terminal shaft 106 to the end of working end 107 measured along a center line extending from the center of handle 103 may be about 1¼ inch.

As illustrated in FIG. 10, the length of handle 109 of Gracey Curette 15/16 108 is in the range of about 3⁷⁄₁₆ inches to about 3¹⁵⁄₁₆ inches, in certain embodiments in the range of about 3.6 inches to about 3.9 inches, more preferably about 3.85 inches. Handle 109 has a diameter that ranges from about ¼ inches to about ¾ inches, in certain embodiments in the range of about 0.25 to about 0.50, more preferably about 0.36 inches. The length of the functional shank from the front of terminal shaft 110 to the end of working end 111 measured along a center line extending from the center of handle may be about 1¼ inch. The length of the functional shank from the front of terminal shaft 112 to the end of working end 113 measured along a center line extending from the center of handle 109 may be about 1¼ inch.

In FIG. 11, the length of handle 115 of Gracey Curette #17/18 116 is in the range of about 3⁷⁄₁₆ inches to about 3¹⁵⁄₁₆ inches, in certain embodiments in the range of about 3.6 inches to about 3.9 inches, more preferably about 3.85 inches. Handle 115 has a diameter that ranges from about ¼ inches to about ¾ inches, in certain embodiments in the range of about 0.25 to about 0.50, more preferably about 0.36 inches. The length of the functional shank from the front of terminal shaft 116 to the end of working end 117 measured along a center line extending from the center of handle may be about 1¼ inch. The length of the functional shank from the front of terminal shaft 118 to the end of working end 119 measured along a center line extending from the center of handle 115 falls may be about 1¼ inch.

Figure 12:
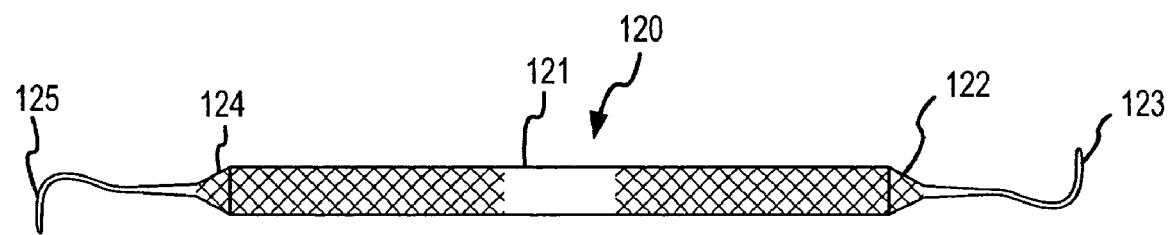
FIG. 12 is a front view of an H6/H7 Scaler dental instrument in accordance with another embodiment of the present invention.
Figure 13:
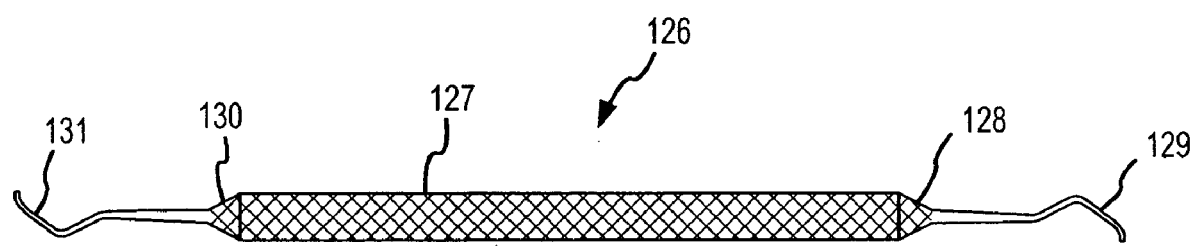
FIG. 13 is a front view of a CO 13/14 dental instrument in accordance with another embodiment of the present invention.
Figure 14:
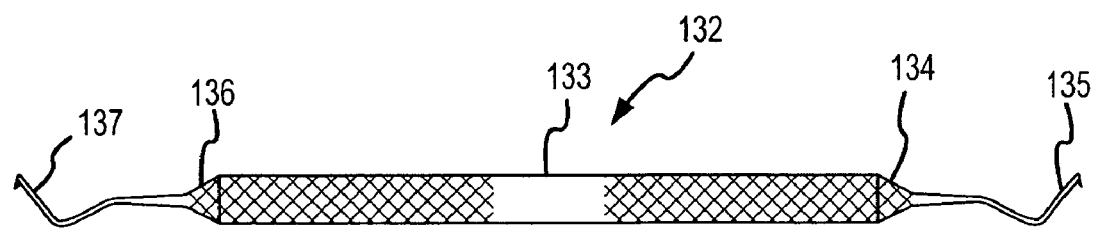
FIG. 14 is a front view of a #204S Sickle Scaler dental instrument in accordance with another embodiment of the present invention.
Figure 15:
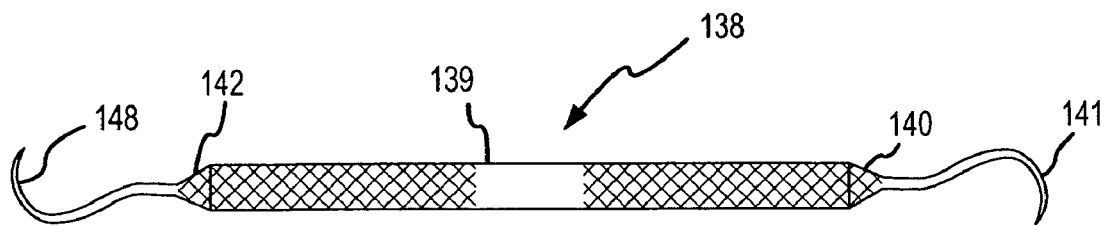
FIG. 15 is a front view of a #17/18 Curette dental instrument in accordance with another embodiment of the present invention.
Figure 16:
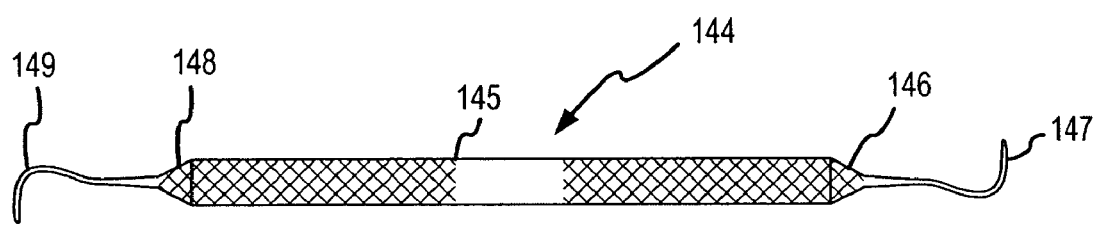
FIG. 16 is a front view of an SH 6/7 dental instrument in accordance with another embodiment of the present invention.
Figure 17:
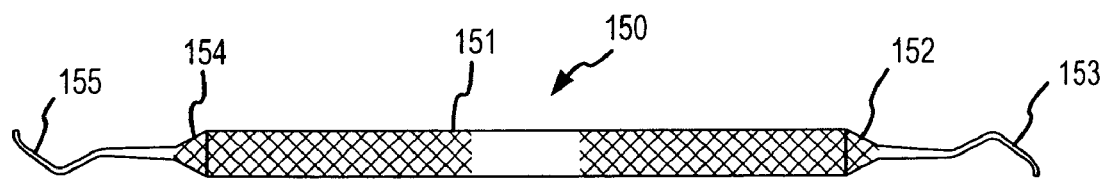
FIG. 17 is a front view of an SB 5/6 dental instrument in accordance with another embodiment of the present invention.
Figure 18:
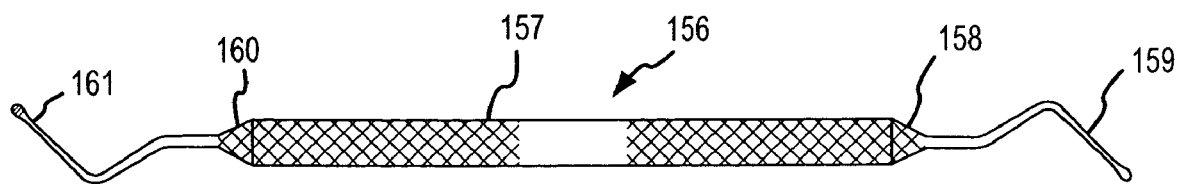
FIG. 18 is a front view of a Hirschfeld DE File dental instrument in accordance with another embodiment of the present invention.

FIG. 12 illustrates an H6/H7 Scaler, FIG. 13 illustrates a CO 13/14, FIG. 14 illustrates a #204S Sickle Scaler, FIG. 15 illustrates a #17/18 Curette, FIG. 16 illustrates an SH 6/7, FIG. 17 illustrates an SB 5/6 and FIG. 18 illustrates a Hirschfeld DE File in accordance with the present invention. The general description of the elements for each is identical to the Gracey 1/2 illustrated in FIG. 6 and will not be repeated. The dimensions and/or use of each are different and therefore are described in further detail.

The sickle scaler, primarily used for supragingival calculus removal, is a very useful instrument. It is often the first instrument used to remove large, heavy deposits thus improving access to subgingival area for other instruments. All sickle scalers have common features making them suited to the removal of heavy calculus deposits and working interproximally, around the contact areas of teeth.

In FIG. 12, the length of handle 121 of H6/H7 Scaler 120 is in the range of about 3⁷⁄₁₆ inches to about 3¹⁵⁄₁₆ inches, in certain embodiments in the range of about 3.6 inches to about 3.9 inches, more preferably about 3.73 inches. Handle 121 has a diameter that ranges from about ¼ inches to about ¾ inches, in certain embodiments in the range of about 0.25 to about 0.50, more preferably about 0.36 inches. The length of the functional shank from the front of terminal shaft 122 to the end of working end 123 measured along a center line extending from the center of handle may be about 1 inch. The length of the functional shank from the front of terminal shaft 124 to the end of working end 125 measured along a center line extending from the center of handle 121 may be about 1 inch.

As shown in FIG. 13, the length of handle 127 of CO 13/14 126 is in the range of about 3⁷⁄₁₆ inches to about 3¹⁵⁄₁₆ inches, in certain embodiments in the range of about 3.6 inches to about 3.9 inches, more preferably about 3.85 inches. Handle 127 has a diameter that ranges from about ¼ inches to about ¾ inches, in certain embodiments in the range of about 0.25 to about 0.50, more preferably about 0.36 inches. The length of the functional shank from the front of terminal shaft 128 to the end of working end 129 measured along a center line extending from the center of handle 127 may fall in a range from about 1 inch to about 1⅞ inches, and may be about 1¼ inch. The length of the functional shank from the front of terminal shaft 130 to the end of working end 131 measured along a center line extending from the center of handle 127 may fall in a range from about 1 inch to about 1⅞ inches, and may be about 1¼ inch.

As shown in FIG. 14, the length of handle 133 of #204S Sickle Scaler 132 is in the range of about 3⁷⁄₁₆ inches to about 3¹⁵⁄₁₆ inches, in certain embodiments in the range of about 3.6 inches to about 3.9 inches, more preferably about 3.85 inches. Handle 133 has a diameter that ranges from about ¼ inches to about ¾ inches, in certain embodiments in the range of about 0.25 to about 0.50, more preferably about 0.36 inches. The length of the functional shank from the front of terminal shaft 134 to the end of working end 135 measured along a center line extending from the center of handle 133 may fall in a range from about ¹⁵⁄₁₆ inches to about 1½ inches, and may be about 1¼ inch. The length of the functional shank from the front of terminal shaft 36 to the end of working end 137 measured along a center line extending from the center of handle 133 may fall in a range from about ¹⁵⁄₁₆ inches to about 1½ inches, and may be about 1¼ inch.

As illustrated in FIG. 15, the length of handle 139 of #17/18 Curette 138 is in the range of about 3⁷⁄₁₆ inches to about 3¹⁵⁄₁₆ inches, in certain embodiments in the range of about 3.6 inches to about 3.9 inches, more preferably about 3.85 inches. Handle 139 has a diameter that ranges from about ¼ inches to about ¾ inches, in certain embodiments in the range of about 0.25 to about 0.50, more preferably about 0.36 inches. The length of the functional shank from the front of terminal shaft 140 to the end of working end 141 measured along a center line extending from the center of handle 139 may fall in a range from about ¹⁵⁄₁₆ inches to about 1³⁄₁₆ inches, and may be about 1¼ inch. The length of the functional shank from the front of terminal shaft 142 to the end of working end 143 measured along a center line extending from the center of handle 139 may fall in a range from about ¹⁵⁄₁₆ inches to about 1³⁄₁₆ inches, and may be about 1¼ inch.

In FIG. 16, the length of handle 145 of S/H 6/7 144 is in the range of about 3⁷⁄₁₆ inches to about 3¹⁵⁄₁₆ inches, in certain embodiments in the range of about 3.6 inches to about 3.85 inches, more preferably about 3.73 inches.

Handle 145 has a diameter that ranges from about ¼ inches to about ¾ inches, in certain embodiments in the range of about 0.25 to about 0.50, more preferably about 0.36 inches. The length of the functional shank from the front of terminal shaft 146 to the end of working end 147 measured along a center line extending from the center of handle 145 may fall in a range from about $^{15}/_{16}$ inches to about 1¼ inches, and may be about 1 inch. The length of the functional shank from the front of terminal shaft 148 to the end of working end 149 measured along a center line extending from the center of handle 145 may fall in a range from about $^{15}/_{16}$ inches to about 1¼ inches, and may be about 1 inch.

In FIG. 17, the length of handle 151 of S/B 5/6 150 is in the range of about 3$^{7}/_{16}$ inches to about 3$^{15}/_{16}$ inches, in certain embodiments in the range of about 3.6 inches to about 3.9 inches, more preferably about 3.85 inches. Handle 151 has a diameter that ranges from about ¼ inches to about ¾ inches, in certain embodiments in the range of about 0.25 to about 0.50, more preferably about 0.36 inches. The length of the functional shank from the front of terminal shaft 152 to the end of working end 153 measured along a center line extending from the center of handle 151 may fall in a range from about $^{15}/_{16}$ inches to about 1½ inches, and may be about 1¼ inch. The length of the functional shank from the front of terminal shaft 154 to the end of working end 155 measured along a center line extending from the center of handle 151 may fall in a range from about $^{15}/_{16}$ inches to about 1½ inches, and may be 1¼ inch.

In FIG. 18, the length of handle 157 of Hirschfeld DE File 156 is in the range of about 3$^{7}/_{16}$ inches to about 3$^{15}/_{16}$ inches, in certain embodiments in the range of about 3.6 inches to about 3.9 inches, more preferably about 3.85 inches. Handle 157 has a diameter that ranges from about ¼ inches to about ¾ inches, in certain embodiments in the range of about 0.25 to about 0.50, more preferably about 0.36 inches. The length of the functional shank from the front of terminal shaft 158 to the end of working end 159 measured along a center line extending from the center of handle 157 may fall in a range from about $^{15}/_{16}$ inches to about 1¼ inches, and may be about 1 inch. The length of the functional shank from the front of terminal shaft 160 to the end of working end 161 measured along a center line extending from the center of handle 157 may fall in a range from about $^{15}/_{16}$ inches to about 1¼ inches, and may be about 1 inch.

II. Restorative Dental Instruments

FIGS. 19-35 illustrate various restorative dental instruments in accordance with aspects of the present invention. The functional shanks in these embodiments may be attached using the techniques described in FIGS. 32-35.

Figure 19:
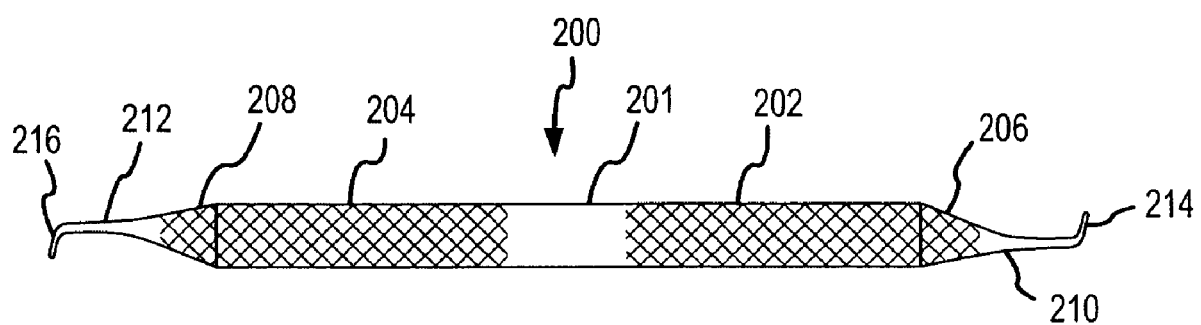
FIG. 19 is a front view of a Carver dental instrument in accordance with another embodiment of the present invention.

FIG. 19 illustrates a Carver 200 in accordance with the present invention. In operation, Carver 200 carves fillings in the mouth of a patient. Carver 200 has a handle 201 with a knurling pattern 202, 204 molded into each end of the handle 201. A first terminal shaft 206 is located at a first end of handle 201 and a second terminal shaft 208 is located at a second end of handle 201. Shank 210 is securely engaged to terminal shaft 206 and shank 212 is securely engaged to terminal shaft 208. Working end 214 is coupled to shank 206 and working end 216 is coupled to shank 212. The combination of terminal shaft 206, working end 214 and shank 210 make up a first end portion. The combination of terminal shaft 208, working end 216 and shank 212 make up a second end portion.

A functional shank is defined by the area extending from the tip of working ends 214, 216 to last bend on shanks 210, 212, which occurs immediately after terminal shafts 206, 208. In an alternative embodiment, the functional shank may extend into terminal shaft 206, 208 to thereby securely engage the function shank to terminal shaft 206, 208 (not shown). A terminal shank is defined by the area beginning below working ends 214, 216 extending to the first bend after terminal shafts 206, 208 respectively. Again, the terminal shank may alternatively extend into terminal shaft 206, 208 to thereby securely engage the function shank to terminal shaft 206, 208 (not shown). In operation, short functional shanks are generally used on coronal surfaces, and long functional shanks are generally used on coronal and root surfaces. The shape and rigidity of shanks 210, 212 determine access of working end 214, 216 for its use. Working ends 214, 216 define the use and function of the Carver 200.

Terminal shafts 206, 208 have a knurling pattern that extends from the handle 201 to shanks 210, 212 respectively. The knurling pattern on terminal shafts 206, 208 improves the dental professional's grip on the Carver 200. An angle α is formed between a line extending from the back end to the front end of terminal shaft 206 and a line extending from handle 201. Angle α ranges from about 5 degrees to about 45 degrees, more preferably from about 5 degrees to about 15 degrees and in one option about 10 degrees. An angle β is formed between a line extending from the back end to the front end of terminal shaft 208 and a line extending from handle 201. Angle β ranges from about 5 degrees to about 45 degrees, more preferably from about 5 degrees to about 15 degrees and in one option about 10 degrees.

The weight, diameter, handle length and surface texture of Carver 200 contributes to its ergonomic properties. Preferably, handle 201 of Carver 200 is hollow since a hollow handle is lighter, resulting in less fatigue and increased intensity of vibrations to fingers of the dental professional. Handle 201 may also be a solid metal without reducing the effectiveness of the ergonomic properties of the present invention. A large diameter of handle 201 is easier to control reducing muscle cramps. A surface of handle 201 having grooves and ridges is easier to control and lends itself to less repetitive stress injury.

The length of handle 201 of Carver 200 is in the range of about 3$^{7}/_{16}$ inches to about 3$^{15}/_{16}$ inches, in certain embodiments in the range of about 3.6 inches to about 3.9 inches, more preferably about 3.85 inches. Handle 201 has a diameter that ranges from about ¼ inches to about ¾ inches, in certain embodiments in the range of about 0.25 to about 0.50, more preferably about 0.36 inches. The length of the functional shank from the front of terminal shaft 206 to the end of working end 214 measured along a center line extending from the center of handle 201 may fall in a range from about $^{13}/_{16}$ inches to about 1$^{5}/_{16}$ inches, and may be one inch. The length of the functional shank from the front of terminal shaft 208 to the end of working end 216 measured along a center line extending from the center of handle 201 may fall in a range from about $^{13}/_{16}$ inches to about 1$^{5}/_{16}$ inches, and may be one inch.

The firm but light hold a dental clinician has on their instruments is referred to as "grasp." A proper grasp enables the clinician to maneuver the instrument around the tooth and correctly direct pressure application for calculus removal without damaging the periodontal tissues. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 201 of Carver 200 at the knurling pattern 202, 204 molded into handle 201 using a modified pen grasp. The thumb and index finger of the clinician are at an opposing position on the handle 201 at junction of handle 201 and terminal shaft 206, 208. Handle 201 is between junction of the first and second joint of the index finger. The pad of the middle finger rests against the shank 210, 212 (side of pad). The fingers of the clinician operate as a "unit."

Continuing with the operation of Carver 200, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke.

Figure 20:
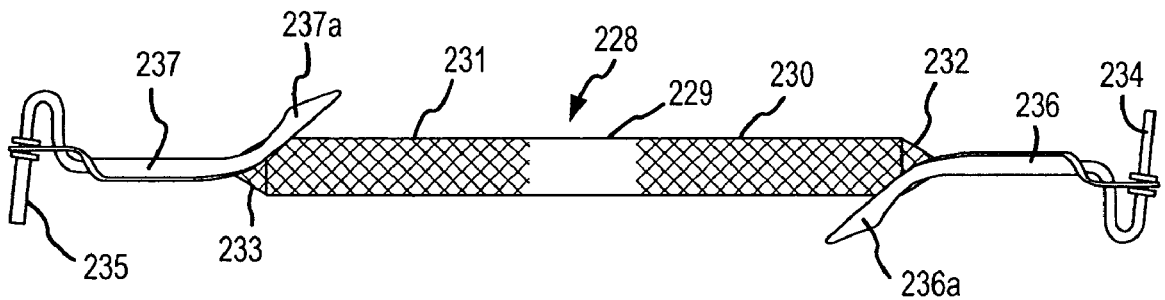
FIG. 20 is a front view of an Amalgam Carrier Regular/Mini Double Ended dental instrument in accordance with another embodiment of the present invention.
Figure 21:
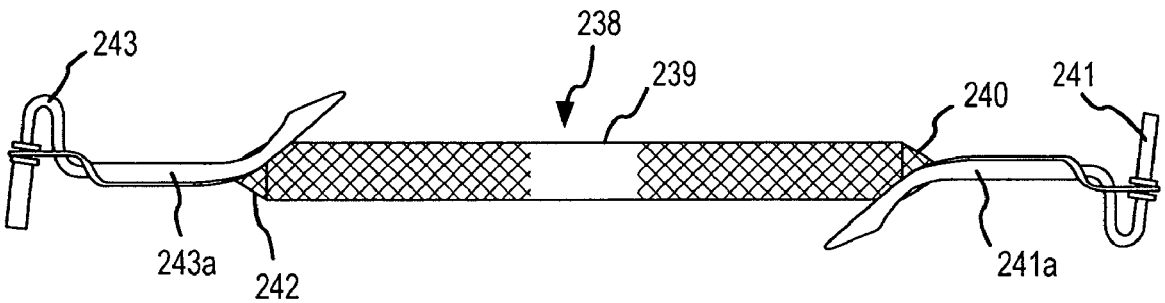
FIG. 21 is front view of an Amalgam Carrier Large/Regular double ended dental instrument in accordance with another embodiment of the present invention.
Figure 22:
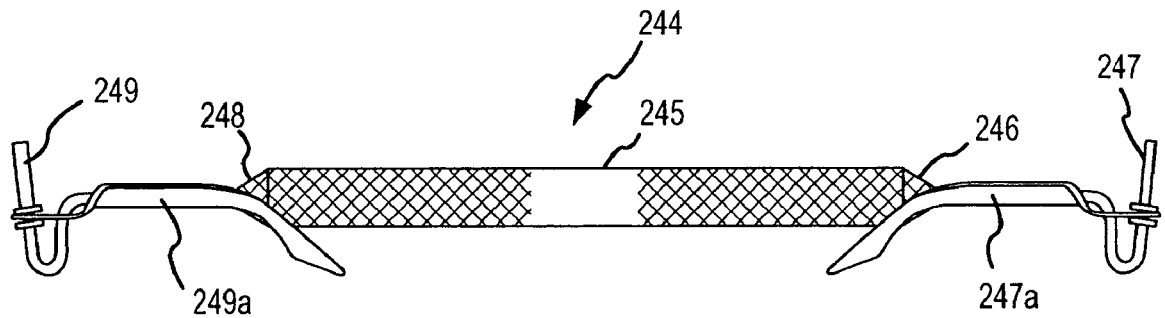
FIG. 22 is front view of an Amalgam Carrier Regular/Mini Double Ended dental instrument in accordance with another embodiment of the present invention.
Figure 23:
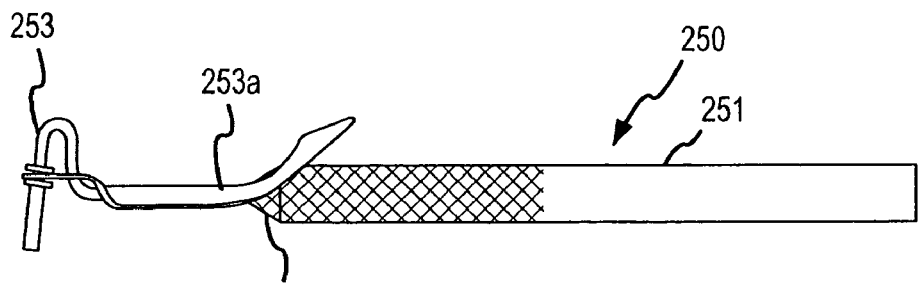
FIG. 23 is a front view of an Amalgam Carrier Regular Single Ended dental instrument in accordance with another embodiment of the present invention.

FIG. 20 is an Amalgam Carrier Regular/Mini Double Ended dental instrument, FIG. 21 is an Amalgam Carrier Large/Regular Double Ended dental instrument, FIG. 22 is an Amalgam Carrier Regular/Mini Double Ended dental instrument with the ends facing the same direction and FIG. 23 is an Amalgam Carrier Regular Single Ended dental instrument in accordance with another embodiment of the present invention. All four embodiments have the same description and dimensions so the description will be done a single time and incorporated into the remaining three. The use for each of the four embodiments varies and thus will be explained in greater detail.

FIG. 20 illustrates an Amalgam Carrier Regular/Mini Double Ended dental instrument 228 in accordance with the present invention. In operation, Amalgam Carrier 228 carves fillings in the mouth of a patient. Carrier 228 has a handle 229 with a knurling pattern 230, 231 molded into each end of the handle 229. A first terminal shaft 232 is located at a first end of handle 229 and a second terminal shaft 233 is located at a second end of handle 229. Shank 236 is securely engaged to terminal shaft 232 and shank 236 is securely engaged to terminal shaft 233. Working end 234 is coupled to shank 236 and working end 235 is coupled to shank 236. The combination of terminal shaft 232, working end 234 and shank 236 make up a first end portion. The combination of terminal shaft 233, working end 235 and shank 236 make up a second end portion.

A functional shank is defined by the area extending from the tip of working ends 234, 235 to last bend on shanks 236, 237, which occurs immediately after terminal shafts 232, 233. In an alternative embodiment, the functional shank may extend into terminal shaft 232, 233 to thereby securely engage the function shank to terminal shaft 232, 233 (not shown). A terminal shank is defined by the area beginning below working ends 234, 235 extending to the first bend after terminal shafts 232, 233 respectively. Again, the terminal shank may alternatively extend into terminal shaft 56, 58 to thereby securely engage the function shank to terminal shaft 232, 233 (not shown). In operation, short functional shanks are used on coronal surfaces and long functional shanks are used on coronal and root surfaces. The shape and rigidity of shanks 236, 237 determine access of working end 234, 235 for its use. Working ends 234, 235 define the use and function of the Amalgam Carrier 228.

Terminal shafts 232, 233 have a knurling pattern that extends from the handle 229 to shanks 236, 237 respectively. The knurling pattern on terminal shafts 232, 233 improves the dental professional's grip on the Amalgam Carrier 228. An angle $\alpha$ is formed between a line extending from the back end to the front end of terminal shaft 236 and a line extending from handle 229. Angle $\alpha$ ranges from about 5 degrees to about 45 degrees, more preferably from about 5 degrees to about 15 degrees and in one option about 10 degrees. An angle $\beta$ is formed between a line extending from the back end to the front end of terminal shaft 233 and a line extending from handle 229. Angle $\beta$ ranges from about 5 degrees to about 45 degrees, more preferably from about 5 degrees to about 15 degrees and in one option about 10 degrees.

The weight, diameter, handle length and surface texture of Amalgam Carrier 228 contributes to its ergonomic properties. Preferably, handle 229 of Amalgam Carrier 228 is hollow since a hollow handle is lighter, resulting in less fatigue and increased intensity of vibrations to fingers of the dental professional. Handle 229 may also be a solid metal without reducing the effectiveness of the ergonomic properties of the present invention. A large diameter of handle 229 is easier to control reducing muscle cramps. A surface of handle 229 having grooves and ridges is easier to control and lends itself to less repetitive stress injury.

The length of handle 229 of Amalgam Carrier 228 is in the range of about 3 3/16 inches to about 3 11/16 inches. More preferably, handle 229 is in the range of about 3 1/4 inches to about 3.9 inches, and in one embodiment about 3.85 inches. Handle 229 has a diameter that ranges from about 1/4 inches to about 3/4 inches, in certain embodiments in the range of about 0.25 to about 0.50, more preferably about 0.36 inches. The length of the functional shank from the front of terminal shaft 232 to the end of working end 234 measured along a center line extending from the center of handle 229 may fall in a range from about 3/4 inches to about 1 1/2 inches, and may be 1 inch. The length of the functional shank from the front of terminal shaft 233 to the end of working end 235 measured along a center line extending from the center of handle 229 may fall in a range from about 3/4 inches to about 1 1/2 inches, and may be 1 inch. Dental instrument 228 also includes a pair of levers 236a and 237a that are used to discharge materials from ends 234 and 235. Levers 236a and 237a are shorter than levers currently available. The length of levers 236a and 237a lie within a range of about 1 1/4 inch to about 2 inches, and are preferably within a range of about 1 1/2 inch to about 1 3/4 inch.

The firm but light hold a dental clinician has on their instruments is referred to as "grasp." A proper grasp enables the clinician to maneuver the instrument around the tooth and correctly direct pressure application for calculus removal without damaging the periodontal tissues. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 229 of Amalgam Carrier 228 at the knurling pattern 230, 231 molded into handle 229 using a modified pen grasp. The thumb and index finger of the clinician are at an opposing position on the handle 229 at junction of handle 229 and terminal shaft 232, 233. Handle 229 is between junction of the first and second joint of the index finger. The pad of the middle finger rests against the shank 236, 237 (side of pad). The fingers of the clinician operate as a "unit."

Continuing with the operation of Amalgam Carrier 228, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke. When material in end 234 or 235 is needed, levers 236a or 236b are depressed.

As shown in FIG. 21, the length of handle 239 of Amalgam Carrier Large/Regular Double Ended dental instrument 238 is in the range of about 3 3/16 inches to about 3 2/3 inches. More preferably, handle 239 is in the range of about 3 1/4 inches to about 3.9 inches, and in some cases about 3.85 inches. Handle 239 has a diameter that ranges from about 1/4 inches to about 3/4 inches, in certain embodiments in the range of about 0.25 to about 0.50, more preferably about 0.36 inches. The length of the functional shank from the front of terminal shaft 240 to the end of working end 241 measured along a center line extending from the center of handle 239 may fall in a range from about 3/4 inches to about 1 1/2 inches, and may be 1 inch. The length of the functional shank from the front of terminal shaft 242 to the end of working end 243 measured along a center line extending from the center of handle 239 may fall in a range from about 3/4 inches to about 1 1/2 inches, and may be 1 inch. Dental instrument 238 includes a pair of levers 241a and 243a that are used to discharge materials from ends 241 and 243. Levers 241a and 243a are shorter than levers currently available. The length of the levers 241a and 243a lie within a range of about 1 1/2 inch to about 2 inches, and are preferably within a range of about 1 1/2 inch to about 1 3/4 inch.

As shown in FIG. 22, the length of handle 245 of Amalgam Carrier Regular/Mini Double Ended dental instrument 244 is in the range of about 3 3/16 inches to about 3 15/16 inches. More preferably, handle 245 is in the range of about 3 1/4 inches to about 3.9 and in some cases about 3.85 inches. Handle 245 has a diameter that ranges from about 1/4 inches to about 3/4 inches, in certain embodiments in the range of about 0.25 to about 0.50, more preferably about 0.36 inches. The length of the functional shank from the front of terminal shaft 246 to the end of working end 247 measured along a center line extending from the center of handle 245 may fall in a range from about 3/4 inches to about 1 1/2 inches, and may be 1 inch. The length of the functional shank from the front of terminal shaft 248 to the end of working end 249 measured along a center line extending from the center of handle 245 may fall in a range from about 3/4 inches to about 1 1/2 inches, and may be 1 inch. One important feature of instrument 244 is that ends 247 and 249 face the same direction. Traditional amalgam carriers have ends facing opposing directions. By reducing the handle length, and when used with smaller hands, ends 247 and 249 may be configured to face the same direction. Instrument 244 also includes levers 247a and 249a and are shorter than levers currently available. The length of the levers 247a and 249a lie within a range of about 1 1/4 inch to about 2 inches, and are preferably within a range of about 1 1/2 inch to about 1 3/4 inch.

As illustrated in FIG. 23, the length of handle 251 of Amalgam Carrier Regular Single Ended dental instrument 250 is in the range of about 3 3/16 inches to about 3 11 15/16 inches. More preferably, handle 251 is in the range of about 3 1/4 inches to about 3.9 inches and in some cases about 3.85. Handle 251 has a diameter that ranges from about 1/4 inches to about 3/4 inches, in certain embodiments in the range of about 0.25 to about 0.50, more preferably about 0.36 inches. The length of the functional shank from the front of terminal shaft 252 to the end of working end 253 measured along a center line extending from the center of handle 251 may fall in a range from about 3/4 inches to about 1 1/2 inches, and may be 1 inch. Instrument 250 includes a lever 253a that is shorter than levers currently available. The length of the lever 253a lies within a range of about 1 1/4 inch to about 2 inches, and are preferably within a range of about 1 1/2 inch to about 1 3/4 inch.

Figure 24:
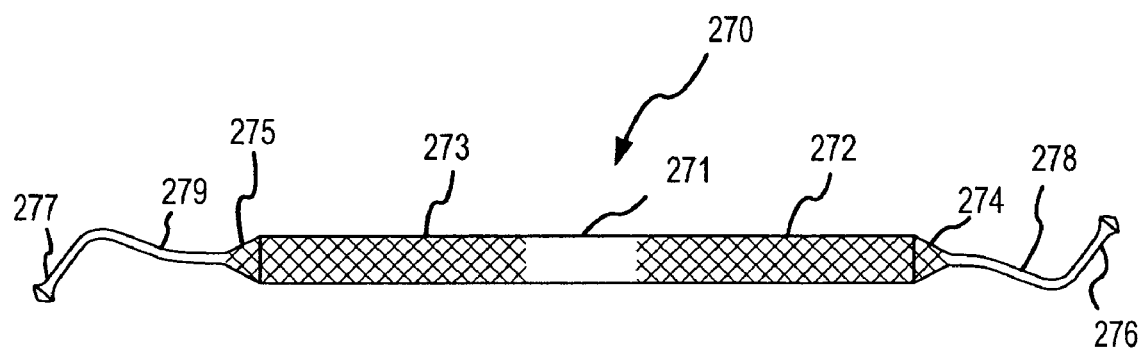
FIG. 24 is a front view of an Acorn Burnisher 21B dental instrument in accordance with another embodiment of the present invention.

FIG. 24 illustrates an Acorn Burnisher 21B dental instrument 270. In operation, Acorn Burnisher 270 polishes and smoothes fillings in a tooth, and is used for anatomical contouring. Acorn Burnisher 270 has a handle 271 with a knurling pattern 272, 273 molded into each end of the handle 271. A first terminal shaft 274 is located at a first end of handle 271 and a second terminal shaft 275 is located at a second end of handle 271. Shank 278 is securely engaged to terminal shaft 274 and shank 279 is securely engaged to terminal shaft 275. Working end 276 is coupled to shank 278 and working end 277 is coupled to shank 279. The combination of terminal shaft 274, working end 276 and shank 278 make up a first end portion. The combination of terminal shaft 275, working end 277 and shank 279 make up a second end portion.

A functional shank is defined by the area extending from the tip of working 276, 277 to last bend on shanks 278, 279, which occurs immediately after terminal shafts 274, 275. In an alternative embodiment, the functional shank may extend into terminal shaft 276, 277 to thereby securedly engage the function shank to terminal shaft 276, 277 (not shown). A terminal shank is defined by the area beginning below working ends 276, 277 extending to the first bend after terminal shafts 274, 275 respectively. Again, the terminal shank may alternatively extend into terminal shaft 276, 277 to thereby securely engage the function shank to terminal shaft 276, 277 (not shown). In operation, short functional shanks are generally used on coronal surfaces, and long functional shanks are generally used on coronal and root surfaces. The shape and rigidity of shanks 278, 279 determine access of working end 276, 277 for its use. Working ends 276, 277 define the use and function of the Acorn Burnisher 270.

Terminal shafts 276, 277 have a knurling pattern that extends from a midpoint on the handle 271 to shanks 278, 279 respectively. The knurling pattern on terminal shafts 276, 277 improves the dental professional's grip on the Acorn Burnisher 270. An angle α is formed between a line extending from the back end to the front end of terminal shaft 274 and a line extending from handle 281. Angle α ranges from about 5 degrees to about 45 degrees, more preferably from about 5 degrees to about 15 degrees and in one option about 10 degrees. An angle β is formed between a line extending from the back end to the front end of terminal shaft 279 and a line extending from handle 281. Angle β ranges from about 5 degrees to about 45 degrees, more preferably from about 5 degrees to about 15 degrees and in one option about 10 degrees.

The weight, diameter, handle length and surface texture of Acorn Burnisher 270 contributes to its ergonomic properties. Preferably, handle 271 of Acorn Burnisher 270 is hollow since a hollow handle is lighter, resulting in less fatigue and increased intensity of vibrations to fingers of the dental professional. Handle 271 may also be a solid metal without reducing the effectiveness of the ergonomic properties of the present invention. A large diameter of handle 271 is easier to control reducing muscle cramps. A surface of handle 271 having grooves and ridges is easier to control and lends itself to less repetitive stress injury.

The length of handle 271 of Acorn Burnisher 270 is in the range of about 3$\frac{7}{16}$ inches to about 3$\frac{15}{16}$ inches, in certain embodiments in the range of about 3.6 inches to about 3.9 inches, more preferably about 3.85 inches. Handle 271 has a diameter that ranges from about ¼ inches to about ¾ inches, in certain embodiments in the range of about 0.25 to about 0.50, more preferably about 0.36 inches. The length of the functional shank from the front of terminal shaft 274 to the end of working end 276 measured along a center line extending from the center of handle 271 may fall in a range from about $\frac{15}{16}$ inches to about 1¼ inches, and may be one inch. The length of the functional shank from the front of terminal shaft 275 to the end of working end 277 measured along a center line extending from the center of handle 271 may fall in a range from about $\frac{15}{16}$ inches to about 1¼ inches, and may be one inch.

The firm but light hold a dental clinician has on their instruments is referred to as "grasp." A proper grasp enables the clinician to maneuver the instrument around the tooth. Three specific grasps are used. They are the pen grasp, the modified pen grasp, and the palm-thumb grasp. The modified pen grasp is the most useful. The index finger and thumb hold the instrument handle. The middle finger rests on the instrument shank. The ring finger advances ahead of the other fingers to act as a support for the hand and instrument.

In operation, the dental professional holds handle 271 of Acorn Burnisher 270 at the knurling pattern 272, 273 molded into handle 271 using a modified pen grasp. The thumb and index finger of the clinician are at an opposing position on the handle 271 at junction of handle 271 and terminal shaft 274, 275. Handle 271 is between junction of the first and second joint of the index finger. The pad of the middle finger rests against the shank 278, 279 (side of pad). The fingers of the clinician operate as a "unit."

Continuing with the operation of Acorn Burnisher 270, the dental clinician establishes a fulcrum to properly use the dental instrument. The fulcrum creates stability and control by generating a pivot point from which the instrument stroke is activated. The instrument stroke may be either an assessment stroke or a working stroke. Proper control during the instrument stroke prevents injury to the patient. The dental professional establishes a fulcrum on a stable oral structure such as an occlusal plane, mandible or zygoma. Typically, the dental professional uses his/her ring finger as the fulcrum pivot point.

The fulcrum is established either at an intraoral location if the professional has small hands or an extraoral location if the professional has large hands and fingers that do not fit into the patient's mouth. For an intraoral fulcrum, the clinician establishes the fulcrum as close to working areas as possible, for example approximately two teeth away from the tooth of interest. Typically, the dental professional uses a mandibular arch or maxillary anterior teeth. For an extraoral fulcrum, the professional uses a maxillary arch. In this way, proper wrist motion, either side to side or up and down, can be activated by pivoting the fulcrum finger. The instrument/wrist/forearm complex must act as a unit rocking firmly but smoothly on the fulcrum. Wrist twisting or independent finger movement should be avoided. This would result in pain, muscle fatigue, and inflammation of the ligaments and nerves of the wrist. The wrist should be straight to activate the instrument stroke.

Figure 25:
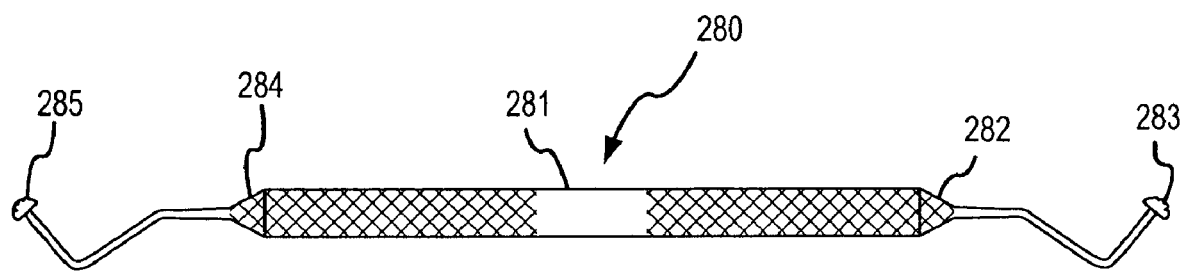
FIG. 25 is a front view of a Packing Instrument R-55 dental instrument in accordance with another embodiment of the present invention.
Figure 27:
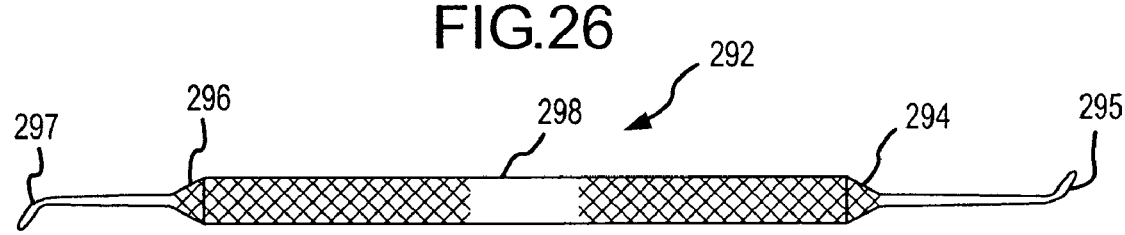
FIG. 27 is a front view of a Cleoid-Discoid dental instrument in accordance with another embodiment of the present invention.
Figure 28:
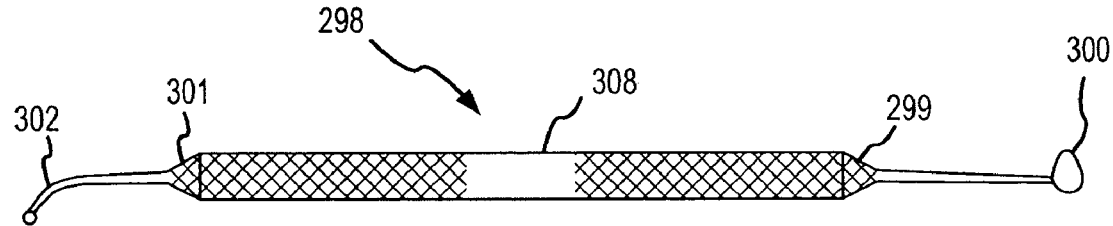
FIG. 28 is a front view of a Burnisher dental instrument in accordance with another embodiment of the present invention.
Figure 29:
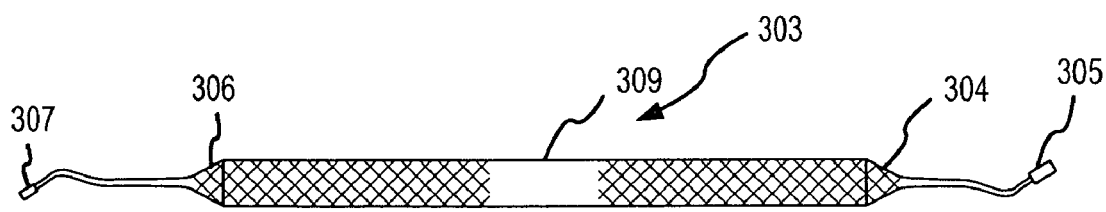
FIG. 29 is a front view of a #1/2 Plugger-Serrated dental instrument in accordance with another embodiment of the present invention.
Figure 30:
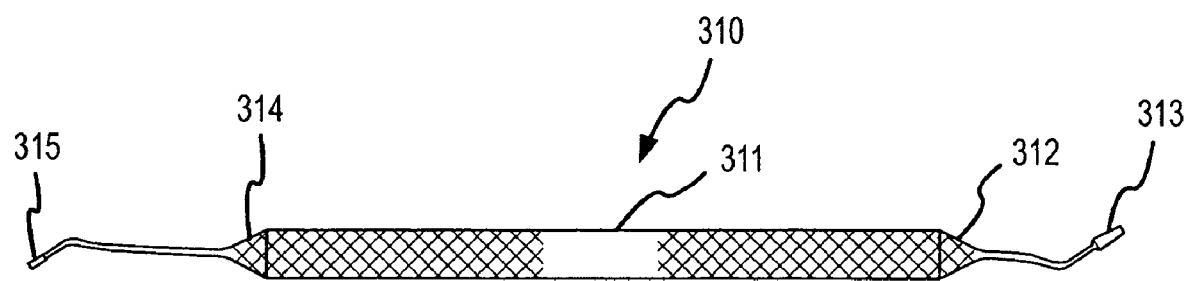
FIG. 30 is a front view of a #1 Hollenbeck Plugger dental instrument in accordance with another embodiment of the present invention.
Figure 31:
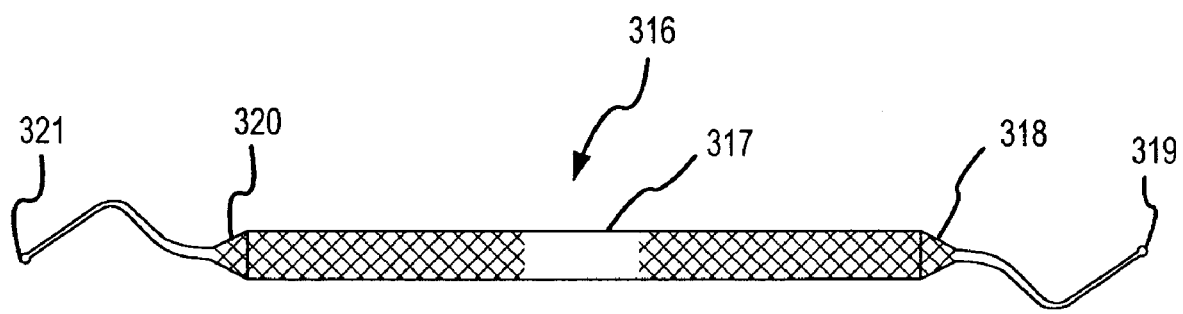
FIG. 31 is a front view of a Spoon Excavator dental instrument in accordance with another embodiment of the present invention.
Figure 32:
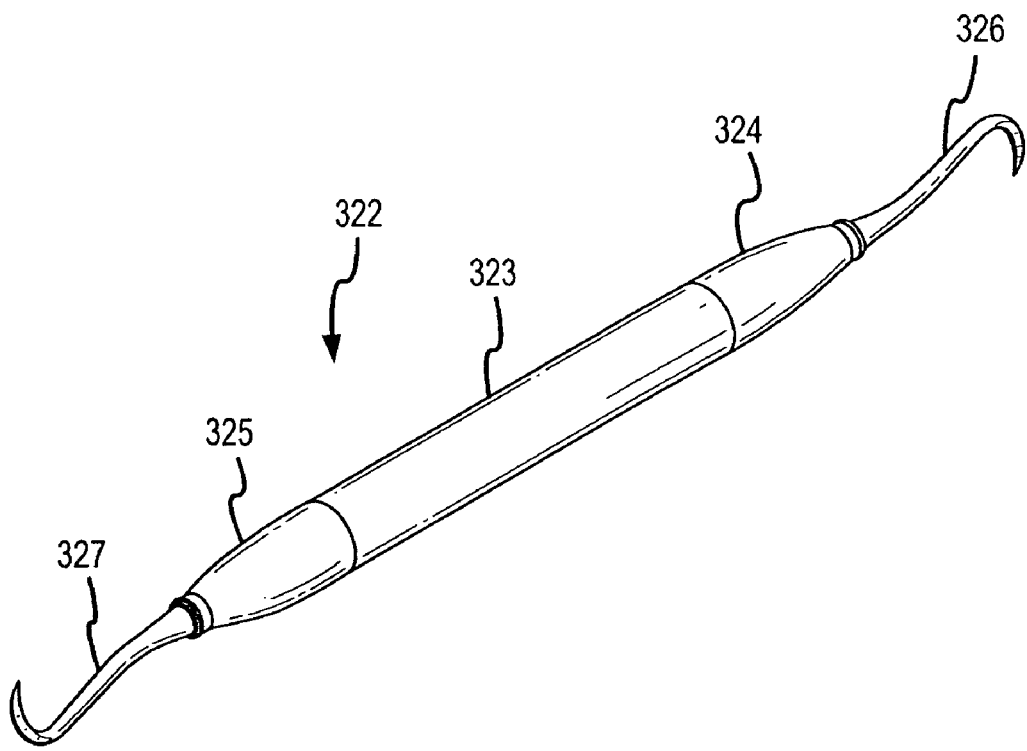
FIG. 32 illustrates an exemplary dental instrument comprising two functional shanks in accordance with one embodiment of the present invention.

FIG. 25 shows a Packing Instrument R-55 dental instrument, FIG. 27 is an Inter-proximal Carver dental instrument, FIG. 28 shows a Cleoid-Discoid dental instrument, FIG. 29 illustrates a Burnisher dental instrument, FIG. 30 shows a #1/2 Plugger-Serrated dental instrument, FIG. 31 is a #1 Hollenbeck Plugger dental instrument and FIG. 32 illustrates a Spoon Excavator dental instrument in accordance with another embodiment of the present invention. The description for each element is similar to the Acorn Burnisher illustrated in FIG. 25 and will not be repeated. The dimensions and use of each are different and therefore are described in further detail.

In FIG. 25, the length of handle 281 of Packing instruments R-55 280 is in the range of about 3$\frac{7}{16}$ inches to about 3$\frac{15}{16}$ inches, in certain embodiments in the range of about 3.6 inches to about 3.9 inches, more preferably about 3.85 inches. Handle 281 has a diameter that ranges from about ¼ inches to about ¾ inches, in certain embodiments in the range of about 0.25 to about 0.50, more preferably about 0.36 inches. The length of the functional shank from the front of terminal shaft 282 to the end of working end 283 measured along a center line extending from the center of handle 281 may fall in a range from about $\frac{15}{16}$ inches to about 1¼ inches, and may be about 1 inch. The length of the functional shank from the front of terminal shaft 284 to the end of working end 285 measured along a center line extending from the center of handle 281 may fall in a range from about $\frac{15}{16}$ inches to about 1¼ inches, and may be about 1 inch. Packing Instruments R-55 280 packs cord along the gum line for crown and bridge work.

Figure 26:
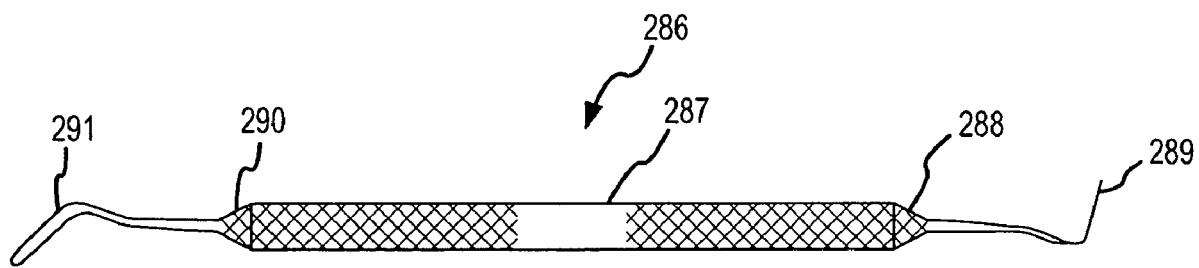
FIG. 26 is a front view of an Inter-proximal Carver dental instrument in accordance with another embodiment of the present invention.

As shown in FIG. 26, the length of handle 287 of Interproximal Carver 286 is in the range of about 3$\frac{7}{16}$ inches to about 3$\frac{15}{16}$ inches, in certain embodiments in the range of about 3.6 inches to about 3.9 inches, more preferably about 3.85 inches. Handle 287 has a diameter that ranges from about ¼ inches to about ¾ inches, in certain embodiments in the range of about 0.25 to about 0.50, more preferably about 0.36 inches. The length of the functional shank from the front of terminal shaft 288 to the end of working end 289 measured along a center line extending from the center of handle 287 may fall in a range from about $^{15}/_{16}$ inches to about 1¼ inches, and may be about 1 inch. The length of the functional shank from the front of terminal shaft 290 to the end of working end 291 measured along a center line extending from the center of handle 287 may fall in a range from about $^{15}/_{16}$ inches to about 1¼ inches, and may be about 1 inch. The Interproximal Carver 286 is used for carving and anatomical finishing of fills.

As shown in FIG. 27, the length of handle 293 of Cleoid-Discoid 292 is in the range of about 3$^{7}/_{16}$ inches to about 3$^{15}/_{16}$ inches, in certain embodiments in the range of about 3.6 inches to about 3.9 inches, more preferably about 3.85 inches. Handle 293 has a diameter that ranges from about ¼ inches to about ¾ inches, in certain embodiments in the range of about 0.25 to about 0.50, more preferably about 0.36 inches. The length of the functional shank from the front of terminal shaft 294 to the end of working end 295 measured along a center line extending from the center of handle 293 may fall in a range from about $^{15}/_{16}$ inches to about 1¼ inches, and may be about 1 inch. The length of the functional shank from the front of terminal shaft 296 to the end of working end 297 measured along a center line extending from the center of handle 293 may fall in a range from about $^{15}/_{16}$ inches to about 1¼ inches, and may be about 1 inch. The Cleoid-Discoid 292 is used for carving and anatomical finishing of fills.

As illustrated in FIG. 28, the length of handle 308 of Burnisher 298 is in the range of about 3$^{7}/_{16}$ inches to about 3$^{15}/_{16}$ inches, in certain embodiments in the range of about 3.6 inches to about 3.9 inches, more preferably about 3.85 inches. Handle 308 has a diameter that ranges from about ¼ inches to about ¾ inches, in certain embodiments in the range of about 0.25 to about 0.50, more preferably about 0.36 inches. The length of the functional shank from the front of terminal shaft 299 to the end of working end 300 measured along a center line extending from the center of handle 308 may fall in a range from about ¾ inches to about 1¼ inches, and may be about 1 inch. The length of the functional shank from the front of terminal shaft 301 to the end of working end 302 measured along a center line extending from the center of handle 308 may fall in a range from about ¾ inches to about 1¼ inches, and may be about 1 inch. The Burnisher 298 is used for carving and anatomical finishing of fills.

In FIG. 29, the length of handle 309 of #1/2 Plugger-Serrated 303 is in the range of about 3$^{7}/_{16}$ inches to about 3$^{15}/_{16}$ inches, in certain embodiments in the range of about 3.6 inches to about 3.9 inches, more preferably about 3.85 inches. Handle 309 has a diameter that ranges from about ¼ inches to about ¾ inches, in certain embodiments in the range of about 0.25 to about 0.50, more preferably about 0.36 inches. The length of the functional shank from the front of terminal shaft 304 to the end of working end 305 measured along a center line extending from the center of handle 309 may fall in a range from about $^{15}/_{16}$ inches to about 1¼ inches, and may be about 1 inch. The length of the functional shank from the front of terminal shaft 306 to the end of working end 307 measured along a center line extending from the center of handle 308 may fall in a range from about $^{15}/_{16}$ inches to about 1¼ inches, and may be about 1 inch. The #1/2 Plugger-Serrated 303 is used for plugging a filling into a preparation.

In FIG. 30, the length of handle 311 of #1 Hollenback Plugger 310 is in the range of about 3$^{7}/_{16}$ inches to about 3$^{15}/_{16}$ inches, in certain embodiments in the range of about 3.6 inches to about 3.9 inches, more preferably about 3.85 inches. Handle 311 has a diameter that ranges from about ¼ inches to about ¾ inches, in certain embodiments in the range of about 0.25 to about 0.50, more preferably about 0.36 inches. The length of the functional shank from the front of terminal shaft 312 to the end of working end 313 measured along a center line extending from the center of handle 311 may fall in a range from about ¾ inches to about 1¼ inches, and may be about 1 inch. The length of the functional shank from the front of terminal shaft 314 to the end of working end 315 measured along a center line extending from the center of handle 311 may fall in a range from about ¾ inches to about 1¼ inches, and may be about 1 inch. The #1 Hollenback Plugger is used for plugging a filling into a preparation.

In FIG. 31, the length of handle 317 of Spoon Excavator 316 is in the range of about 3$^{7}/_{16}$ inches to about 3$^{15}/_{16}$ inches, in certain embodiments in the range of about 3.6 inches to about 3.9 inches, more preferably about 3.85 inches. Handle 317 has a diameter that ranges from about ¼ inches to about ¾ inches, in certain embodiments in the range of about 0.25 to about 0.50, more preferably about 0.36 inches. The length of the functional shank from the front of terminal shaft 318 to the end of working end 319 measured along a center line extending from the center of handle 317 may fall in a range from about $^{15}/_{16}$ inches to about 1¼ inches, and may be about 1 inch. The length of the functional shank from the front of terminal shaft 320 to the end of working end 321 measured along a center line extending from the center of handle 317 may fall in a range from about $^{15}/_{16}$ inches to about 1¼ inches, and may be about 1 inch. Spoon Excavator 316 picks out or takes out tooth decay.

III. Dental Tool Tip to Handle Interface and Attachment

In another aspect of the invention, exemplary tip to handle interfaces of dental instruments, which allow for repeated autoclaving without significant loss of engagement between parts are described. These interfaces may be used with any of the embodiments described herein.

In this regard, the instrument tip may be securely engaged with the handle of the dental instrument via a sweated fit (preferably using tapered parts), achieved by a temperature differential between the mating parts. A sweated fit will generally require a close tolerance between the two, interfering parts, and the securing mechanism occurs via small variations in size of mating parts due to heating one and cooling (or not heating) the other. As the parts come to a common temperature, the tolerances converge, and the parts mate to form a sweated fit. The use of tapered parts permits larger tolerances between the mating parts, thus simplifying the manufacturing process.

Figure 33:
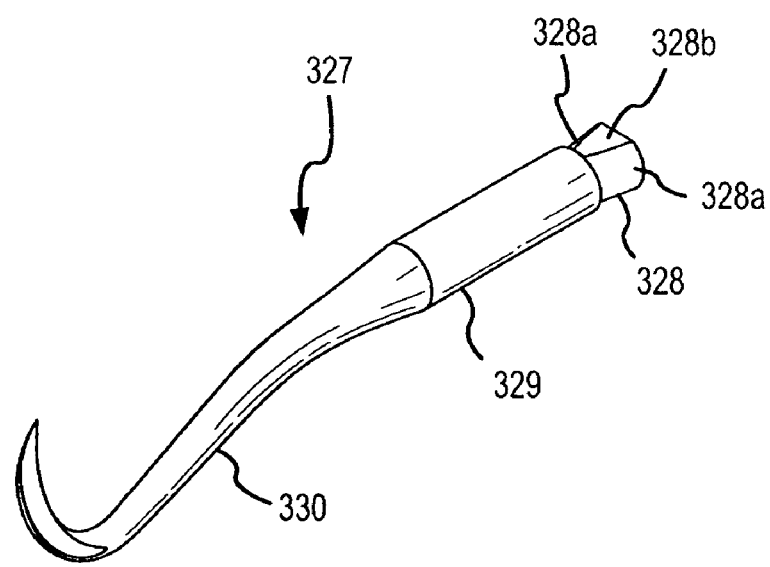
FIG. 33 illustrates an exemplary functional shank in accordance with an embodiment of the present invention.

With reference to FIG. 32, an exemplary dental instrument 322 is illustrated, having handle 323. Dental instrument 322 in one embodiment may be a H6/H7 Scaler dental instrument and may have similar dimensions to those described in connection with FIG. 12. Terminal shafts 324, 325 are located at opposite ends of handle 323 (and may comprise one continuous piece of material along with handle 323), and functional shanks (i.e., instrument tips) 326, 327 are securely engaged to terminal shafts 324, 325, respectively, via a sweated fit. FIG. 33 illustrates a detailed view of a functional shank 327 in accordance with an embodiment of the invention. Function shank 327 includes nub region 328, terminal shank 329, and a working end 330 which provides a surface for cleaning or repairing a tooth. In certain embodiments, nub region 328 may be configured to include angled edges 328a and side flats 328b. Such angled edges and side flats may be configured to provide various interfaces with a fixative, such as glue, to help prevent rotation and pulling out of the handle 323, as described below.

As will be appreciated by those skilled in the art, the description and configurations of FIGS. 32 and 33 are generally applicable to any dental instrument known in the art, including those described with reference to FIGS. 1-31 herein. As such, dental instrument 322 may include knurling patterns, etc., and working end 326, 327 may comprise any known configuration such as those illustrated in FIGS. 1-31.

Figure 34:
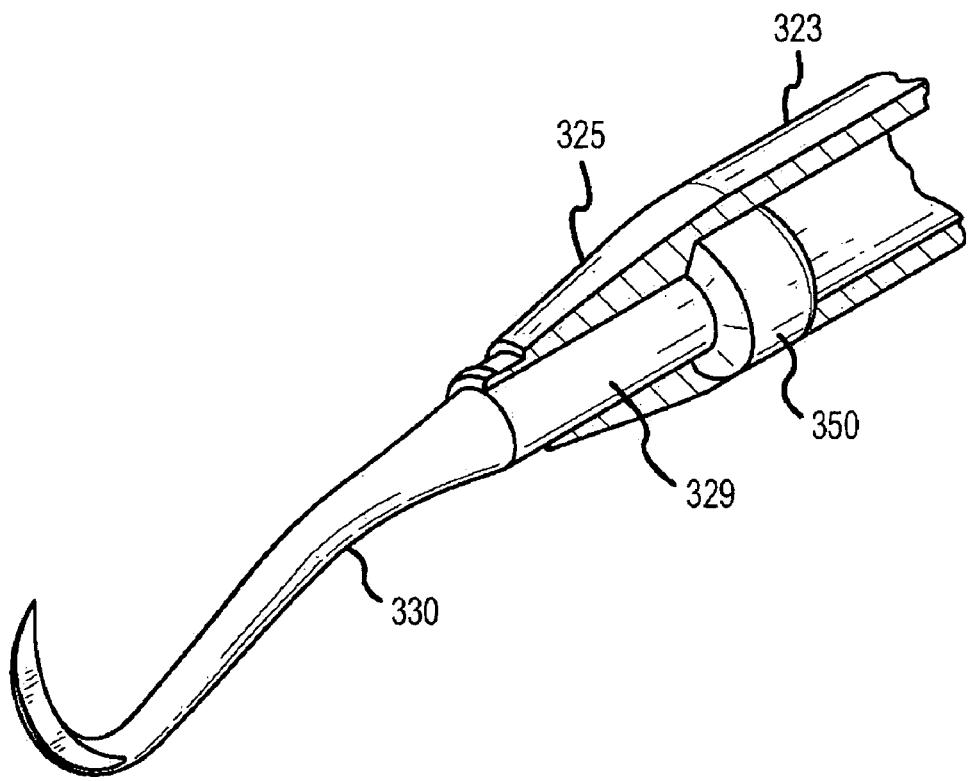
FIG. 34 illustrates a perspective of a functional shank engaged with a terminal shaft and end portion of a dental instrument handle in accordance with one embodiment of the present invention.

FIG. 34 shows functional shank 327 securely engaged with terminal shaft 325 of handle 323 via a sweated fit. Terminal shaft 325 generally includes a hollow interior forming a void which engages terminal shank 327 via a sweated fit. In certain embodiments, a similar configuration may be used to securely engage functional shank 326 to terminal shaft 324 (see FIG. 32). Optionally, a fixative 350, such as a glue, may be used to further secure terminal shaft 325 to shank 327, especially when the dental instrument is heated and cooled, such as during autoclaving.

Figure 35:
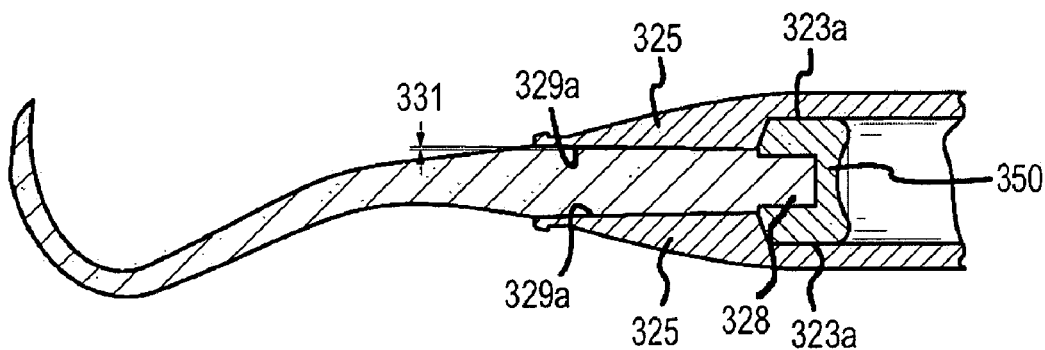
FIG. 35 illustrates a cross-section of the embodiment shown in FIG. 34.

With reference to FIG. 35, in certain embodiments, the interior void of terminal shaft 325 will comprises a tapered wall region 325a, and will generally be configured so as to securely engage the terminal shank 329 of functional shank 327 via a sweated fit. Terminal shank 329 may comprise tapered wall region 329a, corresponding to tapered wall region 325a of terminal shaft 325 within normal tolerances 331 to form the sweated fit. The tapered nature of the interior of shaft 325 and shank 329 is advantageous in that a larger tolerance between the two parts may be used while still ensuring a secure sweat fit. More specifically, because the two parts are angled, shank 329 can be manufactured to tolerances of about 1/1,000 inch while still permitting it to be inserted into shaft after heating. Without such a taper, tighter, difficult to maintain tolerances would be needed. As the two parts cool, shaft 325 compresses about shank 329 to provide the sweat fit. Further, handle 323 may comprise interior aspect 323a configured so as to receive the fixative 350 and nub region 328. Again, as will be appreciated by those skilled in the art, the description and configurations of FIGS. 34 and 35 are generally applicable to any dental instrument known in the art, including those described with reference to FIGS. 1-33 herein.

In certain embodiments, handle 323 is comprised of two symmetrical parts (not shown), connected via a tight press fit sleeve or roll pin. This connector may, in some embodiments, be aluminum so that no dimensional changes to the fitting occurs during autoclaving. The two part handle allows for an opposite facing orientation of the inserted functional shanks 326, 327 during final assembly of dental instrument 322 and an entry point for introduction of the fixative.

In another aspect of the invention, a method for securely engaging a dental instrument tip (e.g., a functional shaft) to a handle is provided. In one embodiment, the method comprises providing a metal handle, e.g., 323 and a functional shank, e.g., 327; heating the metal handle 323; and engaging the terminal shank 329 of functional shaft 327 with the interior void of terminal shaft 325 so as to form a sweated fit between tapered wall region 325a of terminal shaft 325 and tapered wall region 329a of terminal shank 329 as the metal handle 323 and functional shank 327 reach equilibrium temperature. In accordance with the sweated fit approach of the invention, when the handle is heated, it expands and receives the functional shank, which may optionally be cooled if desired. When the parts reach room temperature they are securely locked together. In certain embodiments, nub region 328 may also be surrounded with a fixative 350, applied after parts have come to room temperature. The mechanical surfaces of the numb region 328 may help to prevent movement of the shank 329 even if fixative 350 becomes separated from nub region 328 and/or the interior of the handle, such as during autoclaving.

Any suitable metal known in the art for such purposes may be used for the handle and/or the functional shank in accordance with the present invention. By way of non-limiting example, the function shank may be comprised, at least in part, of stainless steel, and the handle may be comprised, at least in part of plated aluminum. As those of skill in the art will recognize, plated aluminum does not generally lend itself well to the tolerances needed for sweated fitting. However, in accordance with the present invention, the tapered wall of the internal void of the terminal shaft allows for greater tolerances. Further, the plating provides a hard surface that bites into the shank to provide a more secure connection. The exterior surface of the handle may also having a plating as desired to obtain the desired finishes.

In one embodiment, after reaching equilibrium temperature, a small amount of a fixative may be applied, e.g., through a small opening or hole in the back of the handle (not shown) to the nub region protruding into the handle. In certain embodiments, nub region may also include a larger hole for receiving the fixative. The fixative thereby attaches to the nub and handle interior aspect to further securedly engage the functional shank to the handle. Any suitable fixative may be used. In certain embodiments, the fixative is a high temperature glue that can compensate for the recurring dimensional differential that results during autoclaving while retaining the bond between the nub region and the interior aspect of the handle during heating and cooling (i.e., the glue is thick enough to stretch and not become detached during the heating cycles).

Those of ordinary skill in the art will realize that specific parameters can vary for different dental instruments and materials of use without departing from the spirit of the invention. Other variations will also be apparent to persons of skill in the art. These equivalents and alternatives are intended to be included within the scope of the present invention. Therefore, the scope of this invention should not be limited to the embodiments described, but should instead be defined by the following claims.

What is claimed is:

1. A dental instrument comprising:
an elongated metal handle having a first end and a second end, the handle having a length in the range of about $3^{7}/_{16}$ inches to about $3^{15}/_{16}$ inches and a diameter in the range of about $\frac{1}{4}$ inches to about $\frac{3}{4}$ inches;
wherein said handle comprises a first terminal shaft having a front end and a back end, the first terminal shaft having a knurling pattern extending from the front end to the back end, wherein the knurling pattern improves the grip on the dental instrument, the back end of the first terminal shaft located at the first end of the handle, the first terminal shaft having an angle μ formed between a line extending along and out of the handle and a line extending along the first terminal shaft from the back end to the front end;
a first terminal shank secured to the first terminal shaft; and a first working end metallically secured to the first terminal shank, wherein the first working end provides an instrument for cleaning or repairing a tooth;

wherein the first terminal shaft is hollow, and the terminal shank is secured to the first terminal shaft via an internal tapered sweated fit.

2. The dental instrument of claim 1, wherein the handle is hollow.

3. The dental instrument of claim 1, wherein the angle μ is in the range of about 5° to about 45°.

4. The dental instrument of claim 1, wherein said first working end comprises a curette blade, sized and configured to scrape deposits from subgingival tooth surfaces.

5. The dental instrument of claim 1, wherein said first working end comprises a hoe, sized and configured to scrape deposits from subgingival tooth surfaces.

6. The dental instrument of claim 1, wherein said first working end comprises a sickle, sized and configured to scrape deposits from subgingival tooth surfaces.

7. The dental instrument of claim 1, wherein said first working end comprises a gracey, sized and configured to scrape deposits from subgingival tooth surfaces.

8. The dental instrument of claim 1, wherein the handle further comprises:

a second terminal shaft having a front end and a back end, the second terminal shaft having a knurling pattern extending from the front end to the back end wherein the knurling pattern improves the grip on the dental instrument, the back end of the second terminal shaft located at the second end of the handle, the second terminal shaft having an angle μ formed between a line extending along and out of the handle and a line extending along the terminal shaft from the back end to the front end; and a second terminal shank secured to the second terminal shaft; and a second working end metallically secured to the terminal shank, wherein the second working end provides an instrument for cleaning or repairing a tooth.

9. The dental instrument of claim 8, wherein the length of the handle is in the range of about 3.6 inches to about 3.9 inches.

10. The dental instrument of claim 8, wherein said second working end comprises a curette blade, sized and configured to scrape deposits from subgingival tooth surfaces.

11. The dental instrument of claim 8, wherein said second working end comprises a hoe, sized and configured to scrape deposits from subgingival tooth surfaces.

12. The dental instrument of claim 8, wherein said second working end comprises a sickle, sized and configured to scrape deposits from subgingival tooth surfaces.

13. The dental instrument of claim 8, wherein said second working end comprises a gracey, sized and configured to scrape deposits from subgingival tooth surfaces.

14. The dental instrument of claim 8, wherein the first end and second end of said handle are formed from separate symmetrical parts, secured via a tight press fit sleeve or roll pin connector.

15. A dental instrument comprising:

an elongated metal handle having a first end portion and a second end portion, the handle having a length in the range of about 3 7/16 inches to about 3 15/16 inches and a diameter in the range of about ¼ inches to about ¾ inches;

wherein at least one end portion of said handle comprises a terminal shaft having a front end and a back end, the terminal shaft having a knurling pattern on its exterior surface extending from the front end to the back end, wherein the knurling pattern improves the grip on the dental instrument, the back end of the terminal shaft located at said at least one end portion, the terminal shaft having an angle μ formed between a line extending along and out of the handle and a line extending along the terminal shaft from the back end to the front end; and at least one functional shank comprising a terminal shank secured to the terminal shaft and a working end metallically secured to the terminal shank, wherein the working end provides an instrument for cleaning or repairing a tooth;

wherein the terminal shaft is hollow, and the terminal shank is secured to the terminal shaft via an internal tapered sweated fit.

16. The dental instrument of claim 15, wherein the angle μ is in the range of about 5° to about 45°, and wherein the handle has a length in the range of about 3.6 inches to about 3.9 inches.

17. The dental instrument of claim 15, wherein both ends of said handle comprise a terminal shaft, and each terminal shaft is secured to a functional shank.

18. The dental instrument of claim 15, wherein the first end portion and the second end portion of said handle are formed from separate symmetrical parts, secured via a tight press fit sleeve or roll pin connector.

19. A dental instrument comprising:

an elongated metal handle having a first end portion and a second end portion, the handle having a length in the range of about 3 7/16 inches to about 3 15/16 inches and a diameter in the range of about ¼ inches to about ¾ inches;

said first end portion and second end portion each comprising a terminal shaft having a front end and a back end;

the terminal shafts each having a knurling pattern on the exterior surface thereof extending from the front end to the back end, wherein the knurling pattern improves the grip on the dental instrument, the back end of the terminal shaft located towards the centerline of the handle, the terminal shaft having an angle μ formed between a line extending along and out of the handle and a line extending along the terminal shaft from the back end to the front end; and the terminal shafts each having a hollow interior forming a void, wherein said interior void comprises a tapered wall region and is configured so as to securely engage the terminal shank of dental instrument tip via a sweated fit.

20. The dental instrument of claim 19, further comprising at least one dental instrument tip comprising a functional shank, wherein said functional shank comprises a terminal shank and a working end metallically secured to the terminal shank, wherein the working end provides an instrument for cleaning or repairing a tooth; and wherein at least one of the terminal shafts of said first or second end portions securely engage the terminal shank of said at least one dental instrument tip via a sweated fit.

21. The dental instrument of claim 20, wherein said terminal shank comprises a tapered region, and said tapered region securely engages said tapered wall region of the interior void of said terminal shaft via a sweated fit.

22. The dental instrument of claim 21, wherein said terminal shank comprises a nub region at the end opposite said working end; wherein each of the first and second end portions of said handle comprise an interior aspect configured to receive said nub region; and wherein said nub region is angled and comprises side flats to thereby provide mechanical surfaces that resist movement when interfaced with a fixative, even when the fixative is separated from the nub region.

23. The dental instrument of claim 21, wherein said dental instrument comprises two of said dental instrument tips, and each of said terminal shafts securely engages the terminal shank of a dental instrument tip via a sweated fit.

24. The dental instrument of claim 23, wherein the first end portion and the second end portion of said handle are formed from separate symmetrical parts, secured via a tight press fit sleeve or roll pin connector.

25. The dental instrument of claim 19, wherein the handle has a length in the range of about 3.6 inches to about 3.9 inches, and each angle $\mu$ is independently in the range of about 5° to about 45°.

26. A method for attaching a dental instrument tip to a dental instrument handle, said method comprising:
providing an elongated metal handle having a first end portion and a second end portion each comprising a terminal shaft having a front end and a back end; the terminal shafts each having a hollow interior forming a void,
wherein said interior void comprises a tapered wall region and is configured so as to securely engage the terminal shank of dental instrument tip via a sweated fit;
providing at least one metal dental instrument tip comprising a functional shank, wherein said functional shank comprises a terminal shank and a working end metallically secured to the terminal shank;
wherein said terminal shank comprises a tapered region configured to securely engage said tapered wall region of the interior void of said terminal shaft via a sweated fit;
heating said metal handle; and
engaging the terminal shank of said at least one dental instrument tip with the interior void of said terminal shaft of one of said first end portion or second end portion of said handle so as to form a sweated fit as the metal handle cools.

27. The method of claim 26, wherein:
said terminal shank further comprises a nub region at the end opposite said working end;
each of the first and second end portions of said handle comprise an interior aspect configured to receive said nub region; and
the interior aspect of said at least one first end portion or second end portion including a fixative.

28. The method of claim 27, wherein said nub region is tapered and comprises side flats to thereby provide mechanical surfaces for interfacing with the fixative.

29. A method for using a dental instrument comprising:
providing a dental instrument having an elongated metal handle having a first end portion and a second end portion, the handle having a length in the range of about $3^{7}/_{16}$ inches to about $3^{15}/_{16}$ inches and a diameter in the range of about $\frac{1}{4}$ inches to about $\frac{3}{4}$ inches; the first end portion comprising a first terminal shaft and the second end portion comprising a second terminal shaft, each having a front end and a back end, the first terminal shaft coupled to a first functional shank at the front end of the first terminal shaft and the second terminal shaft coupled to a second functional shank at the front end of the second terminal shaft, wherein the first terminal shaft is hollow, and the first functional shank is secured to the first terminal shaft via an internal tapered sweated fit;
grasping the dental instrument;
establishing a fulcrum on the interior of the mouth of a patient; and
utilizing proper wrist movement to use the dental instrument, wherein said fulcrum is the pivot point for all movement.

30. The method of claim 29, wherein the grasping of the instrument is effected by the modified pen grasp, wherein the interior of the mouth of a patient is a mandibular arch or maxillary anterior teeth, and wherein the fulcrum is established by the ring finger of a dental professional.

* * * * *